(12) United States Patent
Koskinen et al.

(10) Patent No.: US 11,442,064 B2
(45) Date of Patent: Sep. 13, 2022

(54) MASS SPECTROMETRIC METHODS AND KITS TO IDENTIFY A MICROORGANISM

(71) Applicant: THERMO FISHER SCIENTIFIC OY, Vantaa (FI)

(72) Inventors: Mikko Koskinen, Vantaa (FI); Leena Valmu, Vantaa (FI); Joni Rannisto, Vantaa (FI); Kelly Flook, Bedford, MA (US); Roger Grist, Ninebanks (GB); Anssi Rantakari, Vantaa (FI)

(73) Assignee: Thermo Fisher Scientific OY, Vantaa (FI)

( * ) Notice: Subject to any disclaimer, the term of this patent is extended or adjusted under 35 U.S.C. 154(b) by 97 days.

(21) Appl. No.: 16/328,233

(22) PCT Filed: Aug. 24, 2017

(86) PCT No.: PCT/EP2017/071361

§ 371 (c)(1),
(2) Date: Feb. 25, 2019

(87) PCT Pub. No.: WO2018/037089

PCT Pub. Date: Mar. 1, 2018

(65) Prior Publication Data

US 2019/0212338 A1    Jul. 11, 2019

(30) Foreign Application Priority Data

Aug. 25, 2016 (FI) .................................. 20165634

(51) Int. Cl.
*G01N 33/569* (2006.01)
*G01N 33/68* (2006.01)

(52) U.S. Cl.
CPC ..... *G01N 33/56944* (2013.01); *G01N 33/569* (2013.01); *G01N 33/56911* (2013.01);
(Continued)

(58) Field of Classification Search
CPC ........... G01N 33/569; G01N 33/56911; G01N 33/56916; G01N 33/56938; G01N 33/56961; G01N 33/6848
See application file for complete search history.

(56) References Cited

U.S. PATENT DOCUMENTS 8,569,010 B2 * 10/2013 Maier .................... C12Q 1/04
435/34
9,074,236 B2 * 7/2015 Stephenson, Jr .. G01N 33/6848
(Continued)

FOREIGN PATENT DOCUMENTS

CN         104797939 A     7/2015
WO    WO-2009065580 A1    5/2009
(Continued)

OTHER PUBLICATIONS

Walpurgis, Katja, et al. "Validated hemoglobin-depletion approach for red blood cell lysate proteome analysis by means of 2 D PAGE and Orbitrap MS." Electrophoresis 33.16 (2012): 2537-2545. (Year: 2012).*

(Continued)

*Primary Examiner* — Jennifer Wecker
*Assistant Examiner* — Oyeleye Alexander Alabi
(74) *Attorney, Agent, or Firm* — Thomas F. Cooney; Gregory Howell Kline

(57) ABSTRACT

The present invention includes a novel method and system for identification of microorganisms in samples that proteins and other biological material from non-microorganism sources (e.g., proteins of mammalian origin) that can interfere with identification of the microorganisms. The methods and systems described herein include use of a single-use chromatography medium to purify intact proteins prior to mass spectrometry analysis. The chromatography medium and the methods described herein can rapidly and efficiently remove of a substantial portion of interfering biological material (e.g., mammalian proteins) from a crude cell lysate while preserving high signal strength and removing enough of the interfering protein(s) to allow for identification of the microorganism(s) by mass spectrometry analysis.

24 Claims, 14 Drawing Sheets

(52) U.S. Cl.
CPC . *G01N 33/56916* (2013.01); *G01N 33/56938* (2013.01); *G01N 33/56961* (2013.01); *G01N 33/6848* (2013.01)

(56) References Cited

U.S. PATENT DOCUMENTS

| | | |
|---|---|---|
| 9,696,284 B2 | 7/2017 | Rannisto et al. |
| 2010/0120085 A1* | 5/2010 | Hyman .................. C12Q 1/04 435/34 |
| 2013/0045532 A1 | 2/2013 | Hyman et al. |
| 2013/0109590 A1 | 5/2013 | Clarizia et al. |

FOREIGN PATENT DOCUMENTS

| | | | |
|---|---|---|---|
| WO | WO-2011006911 A2 | 1/2011 | |
| WO | WO-2011124703 A1 | 10/2011 | |
| WO | WO-2012086859 A1 | 6/2012 | |
| WO | 2013/166169 A1 | 11/2013 | |
| WO | WO-2014100456 A1 * | 6/2014 | ............ B01L 3/5027 |

OTHER PUBLICATIONS

Shim, Sang Eun, et al. "Effect of the polymerization parameters on the morphology and spherical particle size of poly (styrene-co-divinylbenzene) prepared by precipitation polymerization." Colloid and Polymer Science 283.1 (2004): 41-48. (Year: 2004).*

Ivanov, Alexander R., Li Zang, and Barry L. Karger. "Low-Attomole Electrospray ionization MS and MS/MS analysis of protein Tryptic digests using 20-µm-iD Polystyrene-Divinylbenzene monolithic capillary columns." Analytical chemistry 75.20 (2003): 5306-5316. (Year: 2003).*

Alvarez-Llamas G., et al., "A novel methodology for the analysis of membrane and cytosolic sub-proteomes of erythrocytes by 2-DE," Electrophoresis, Dec. 2009, vol. 30, No. 23, pp. 4095-4108.

Brgles M., et al., "Selectivity of monolithic supports under overloading conditions and their use for separation of human plasma and isolation of low abundance proteins," Journal of Chromatography A, Apr. 2011, vol. 1218, No. 17, pp. 2389-2395.

FI Application No. 20165634, Search Report dated Mar. 9, 2017, 2 pages.

Freeby S., et al., "Enrichment of Medium- and Low-abundance Proteins in Sample Types Using Proteominer Technology," Bulletin 5916 [online] Bio-Rad Laboratories, Inc., 2010, [retrieved on Jan. 16, 2019], 6 pages, Retrieved from< http://www.biorad.com/webroot/web/pdf/lsr/literature/Bulletin_5916.pdf>.

International Preliminary Report on Patentability for International Application No. PCT/EP2017/071361 dated Feb. 26, 2019, 10 pages.

International Search Report and Written Opinion for Application No. PCT/EP2017/071361, dated Oct. 11, 2017, 14 pages.

Meex C., et al., "Direct identification of bacteria from BacT/ALERT anaerobic positive blood cultures by MALDI-TOF MS: MALDI Sepsityper kit versus an in-house saponin method for bacterial extraction," Journal of Medical Microbiology, Nov. 2012, vol. 61, No. 11, pp. 1511-1516.

Walpurgis K., et al., "Validated hemoglobin-depletion approach for red blood cell lysate proteome analysis by means of 2D PAGE and Orbitrap MS," Electrophoresis, Aug. 2012, vol. 33, No. 16, pp. 2537-2545.

Zheng J., et al., "One-pot synthesis of CuFe2O4 magnetic nanocrystal clusters for highly specific separation of histidine-rich proteins," Journal of Materials Chemistry B, 2014, vol. 2, No. 37, pp. 6207-6214.

Zhu Y., et al., "Sensitive and Fast Identification of Bacteria in Blood Samples by Immunoaffinity Mass Spectrometry for Quick BSI Diagnosis," Chemical Science (Royal Society FO Chemistry), vol. 7, No. 5, May 1, 2016 (May 1, 2016), pp. 2987-2995, XP055410693, London, ISSN: 2041-6520, DOI: 10.1039/C5SC04919A.

Huang et al., "CEC with monolithic poly (styrene-divinylbenzene-vinylsulfonic acid) as the stationary phase", Electrophoresis, 2006, vol. 27, No. 23, pp. 4674-4681.

Ogino et al., "Synthesis of monodisperse macroreticular styrene-divinylbenzene gel particles by a single-step swelling and polymerization method", Journal of Chromatography A, 1995, vol. 699, Nos. 1-2, pp. 59-66.

* cited by examiner

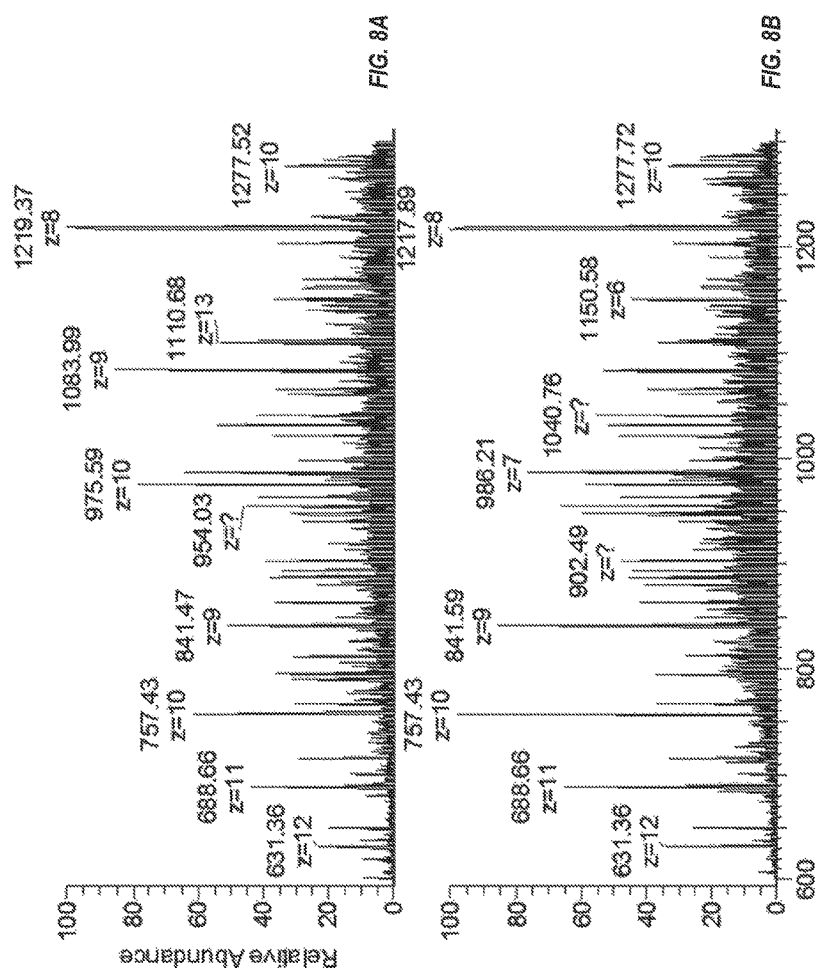

MASS SPECTROMETRIC METHODS AND KITS TO IDENTIFY A MICROORGANISM

CROSS REFERENCE TO RELATED APPLICATIONS

This application is the U.S. National Stage of international application PCT/EP2017/071361, having international filing date Aug. 24, 2017, which claims priority to and the benefit of the filing date of Finland Application No. 20165634, filed Aug. 25, 2016, entitled APPARATUS AND METHODS FOR IDENTIFICATION OF A MIX MICROORGANISM IN AN INTERFERING MATRIX, which is incorporated herein in its entirety.

BACKGROUND

In recent years, mass spectrometry has gained popularity as a tool for identifying microorganisms due to its increased accuracy and shortened time-to-result when compared to traditional methods for identifying microorganisms. To date, the most common mass spectrometry method used for microbial identification is matrix-assisted laser desorption ionization time-of-flight (MALDI-TOF) mass spectrometry. In MALDI-TOF, cells of an unknown microorganism are mixed with a suitable ultraviolet light absorbing matrix solution and are allowed to dry on a sample plate. Alternatively, extract of microbial cells is used instead of the intact cells. After transfer to the ion source of a mass spectrometer, a laser beam is directed to the sample for desorption and ionization of the proteins and time-dependent mass spectral data is collected.

The mass spectrum of a microorganism produced by MALDI-TOF methods reveals a number of peaks from intact peptides, proteins, and protein fragments that constitute the microorganism's "fingerprint". This method relies on the pattern matching of the peaks profile in the mass spectrum of an unknown microorganism to a reference database comprising a collection of spectra for known microorganisms obtained using substantially the same experimental conditions. The better the match between the spectrum of the isolated microorganism and a spectrum in the reference database, the higher the confidence level in identification of the organism at the genus, species, or in some cases, subspecies level. Because the method relies upon matching the patterns of peaks in MALDI-TOF mass spectra, there is no requirement to identify or otherwise characterize the proteins represented in the spectrum of the unknown microorganism in order to identify it.

Several other mass spectrometry methods for detection of microorganisms have been used—these include so-called "bottom-up" and "top-down" methods. In the bottom-up approach, a protein extract may be digested with one or more proteases, followed by one or more dimensions of separation of the peptides by liquid chromatography coupled to mass spectrometry. By comparing the masses of the proteolytic peptides or their tandem mass spectra with those predicted from a database, peptides can be identified and multiple peptide identifications assembled into a protein identification.

In the top-down approach, microorganisms may be identified and, in some cases, quantified by analysis of intact proteins that have not been subjected to enzymatic digestion prior to separation and mass spectrometry. Intact proteins extracted from a microorganism are preferably separated by one or more dimensions of liquid chromatography (although protein extracts can be infused directly into the mass spectrometer in some methods), followed by infusion into a mass spectrometer. Organisms may be identified in a first mass spectrometry step (MS) by determining the intact mass of the a sufficient number of proteins in the extract. In a second mass spectrometry step (MSMS), selected proteins from the first mass spectrometry step may be fragmented in the mass spectrometer—the fragmentation pattern of the proteins may be used to enhance the certainty of the identification in the first step. The main advantages of the top-down approach include the ability to detect degradation products, sequence variants, and combinations of post-translational modifications.

The use of mass spectrometry has revolutionized clinical microbiology and shortened diagnosis times and increased the precision of diagnosis. Nevertheless, mass spectrometry analysis, MALDI-TOF in particular, has not been widely adopted for some clinical samples because these samples include complex matrices (e.g., proteins of mammalian origin) that can impact the reliability and accuracy of the analysis. For instance, blood cultures represent the most urgent and critical sample for the microbiology laboratory. While critical patient care would benefit the most from successful analysis of blood cultures using mass spectrometry (due to significantly faster time to result), this application is currently not widely used because blood culture samples remain the most challenging sample type for mass spectrometry. In fact, MALDI-TOF can typically only deliver very low sensitivity and specificity for positive blood cultures (approximately 70-80%). Other samples with similarly complex matrices (e.g., urine and cerebrospinal fluid) also deliver low sensitivity and specificity. Because the sensitivity of MALDI analysis for samples with complex matrices is so low, there is significant danger of producing false negatives for truly positive samples and, perhaps even worse, false positives for negative samples.

BRIEF SUMMARY

The present invention includes a novel method and system for identification of microorganisms in samples that proteins and other biological material from non-microorganism sources (e.g., proteins of mammalian origin) that can interfere with identification of the microorganisms. Identification of microbes from fluids, tissues, and cultures from patients suspected of having a microbial infection is one of the most critical assays in clinical microbiology and is vital for patient care. Microbes can be identified by mass spectrometry (MS) using intact proteins as analytes, as has been shown using either MALDI-TOF or electrospray ionization (ESI). However, many clinical samples include a very complex and challenging matrix (e.g., mammalian cells, proteins, bodily fluids, media components, etc.) in addition to the target microorganism(s).

In such samples, proteins from the microorganisms needed for identification by mass spectrometry may be extracted, but their signal may be suppressed or overwhelmed by proteins that are in the matrix (e.g., proteins of mammalian origin). One example of a particularly challenging matrix is blood. In patients suspected of having sepsis, rapid identification of the causative microbe can literally mean the difference between life and death. However, when the red blood cells are lysed, hemoglobin binds to the bacterial cells at high concentration and the hemoglobin can carry through into the microbial lysate and can overwhelm the signal for the proteins from the microorganism(s). The challenge is to quickly and efficiently remove enough of the hemoglobin to allow the signal for the microbial proteins to be visible without removing so much protein that the overall signal intensity is too low. Fluids such as, but not limited to, urine and cerebrospinal fluid present similar matrix challenges.

The methods and systems described herein include use of a single-use chromatography medium to purify intact proteins prior to mass spectrometry analysis. Proteins from the microbial extract are bound to the chromatography medium, where they are washed and then eluted for mass spectrometry analysis. Surprisingly and unexpectedly, it has been found that the chromatography medium and the methods described herein can rapidly and efficiently remove of a substantial portion of interfering biological material (e.g., mammalian proteins) from a crude cell lysate while preserving high signal strength and removing enough of the interfering protein(s) to allow for identification of the microorganism(s) by mass spectrometry analysis.

The procedures described herein can be extremely fast. Likewise, the method of the present invention is simple and quick because there is no need for chemical or enzymatic digestion of a sample and data processing is accomplished in real time. Sample preparation from a culture or (assuming sufficiently high microbial load) a bodily fluid or surface swab can be carried out in as little as about 15 minutes (e.g., 15 to 30 minutes). Mass spectrometry analysis can be accomplished within a few minutes, for example, less than 10 minutes, less than 5 minutes or within about one minute or less. Initial mass spectrometry is generally sufficient to identify the microorganism(s) to the genus or species level. Additional mass spectrometry analyses (e.g., targeted MS and $MS^n$) may be called for to further characterize the microorganism identified in the first mass spectrometry step to, for example, identify the microorganism(s) to the strain, subspecies, pathovar or serovar level or, as needed determine virulence factors, antibiotic resistance markers, antibiotic susceptibility markers or other characteristics. This second phase may be performed in within a few minutes, for example, less than 15 minutes, less than 10 minutes or within about five minutes or less. Both phases rely on the detection and identification of intact proteins derived from the microorganisms, without chemical, physical or enzymatic degradation of those proteins to their substituent peptides.

The method is applicable to a variety of different sample types, including samples from pure or mixed culture derived from clinical samples including, without limitation, blood, pus, urine, lacrimal fluid, nasal discharge, lymph, synovial fluid, cerebrospinal fluid, stool, sputum, wound and body site swabs, and to samples derived from other sources including industrial or environmental samples such as food (e.g., meat and dairy samples, fruits, and vegetables), beverage, soil, water (e.g., municipal waste water), air, and swabs of surfaces. And while the following discussion focuses on the identification of microorganisms via the characterization of proteins, the methods and systems discussed herein are equally applicable to the identification of microorganisms via the characterization of one or more of small molecules, lipids, or carbohydrates, and the like.

In acute infections, pathogens are usually present in large numbers. For instance, in the case of inflammation of the urinary tract or kidneys, around $10^5$ to $10^7$ pathogens are present in a milliliter of urine. Since only around $10^3$ to $10^4$ microbes are required for mass spectrometric analysis, centrifuging will immediately yield sufficient quantities of pathogens for mass spectrometric identification.

If more than $10^5$ microbial pathogens are present in the centrifuged sample, the deposited pellets are visible to the naked eye. But even if there are fewer microbial pathogens in the body fluid, fast extraction and decomposition methods can be applied successfully to the then invisible pellets. The extraction processes for the proteins in the pathogens are very fast and add only a few minutes to the total analysis time.

It is also possible to culture the pathogens in the body fluid directly, as, for instance, with the known method of "blood culture" by directly incubating the bag of whole blood. Such culturing is significantly faster than growing cultures in Petri dishes and can, particularly in the case of heavy infections, often provide sufficient pathogens for identification within an hour.

Acute infections can also be caused by non-microbial pathogens like viruses, *Chlamydia* and *Rickettsia*, none of which can be cultured in a nutrient medium, as they can only multiply in host cells. In acute infections, certain forms of these pathogens are found in extremely high numbers in body fluids and can be effectively precipitated in an ultracentrifuge in spite of their small size; they can be identified by their specific proteins measured by mass spectrometry. The methods described herein are not limited to analysis and identification of bacteria and the like. For instance, viruses typically have highly characteristic coat proteins in the form of a capsid that can be identified by mass spectrometry.

In an embodiment of the present disclosure, a method is described for identifying a microorganism in a fluid that includes biological material (e.g., interfering proteins) from a source other than the microorganism. The method described below includes means for enriching the proteins from the microorganism and depleting the interfering biological material so that the microorganism(s) present in the sample can be identified. In one embodiment, the method includes preparing a lysate derived from the fluid, wherein the lysate including proteins derived from the fluid and proteins from the microorganism, and contacting the lysate with a chromatography medium, wherein the proteins derived from the fluid and the proteins from the microorganism bind to the chromatography medium. The method further includes selectively eluting proteins bound to the chromatography medium to produce at least one eluted fraction, and subjecting the at least one eluted fraction to protein mass spectrometry analysis to identify the presence of one or more microorganisms in the fluid. In one embodiment, the at least one eluted fraction is enriched in the proteins from the microorganism and depleted in the proteins derived from the fluid.

In one embodiment, the fluid may be one of blood, a blood culture, urine, or cerebrospinal fluid. In one embodiment, the interfering biological material can be anything in the fluid that can suppress or overwhelm the signal from the proteins of the microorganism. Suitable examples of interfering biological material, which are proteins in this case, include, but are not limited to one or more of hemoglobin, defensins, or proteolysis products thereof.

In another embodiment, a method is disclosed for identifying a microorganism in a fluid that includes interfering mammalian proteins and proteins from the microorganism. In an initial step, the method includes preparing a lysate from the fluid that includes the mammalian proteins and the proteins from the microorganism. In one embodiment, the fluid may be one or more of whole blood, a blood culture, urine, or cerebrospinal fluid. In one embodiment, the lysate is prepared by (a) lysing mammalian cells, if present in the fluid, by contacting the mammalian cells with a lysing agent selected to lyse the mammalian cells but not cells of the microorganism. (b) separating the cells of the microorganism from the lysed mammalian cells, (c) washing the cells of the microorganism, (d) lysing the cells of the microorganism to release the contents thereof, and (e) separating unlysed microorganism cells and cell fragments from the contents of the microorganism cells to yield the lysate.

The method further includes separating proteins derived from the microorganism from the mammalian proteins. The separating includes (a) providing a single use extraction cartridge that contains a bed of a chromatography medium, (b) adding the lysate to the extraction cartridge and allowing the lysate to flow through the bed of chromatography media. (c) washing the extraction cartridge with a wash buffer; and (d) selectively eluting proteins bound to the chromatography medium to produce at least one eluted fraction. In one embodiment, the selectively eluting may include flowing through the bed of chromatography medium different concentrations of an elution buffer that includes a polar organic solvent in a concentration range of 10 vol % to 60 vol %. The method further includes subjecting the at least one eluted fraction to protein mass spectrometry analysis to identify the presence of one or more infectious agent in the blood sample. Suitable example of mass spectrometry analysis techniques include, but are not limited to, MALDI-TOF, ESI-MS, or ESI-MS$^n$ (e.g., MS/MS).

In yet another embodiment, a kit for identifying a microorganism in a fluid sample is disclosed. The kit includes a sample lysis tube comprising a detergent selected for selectively lysing mammalian cells in the sample and not cells of the microorganism to be identified, a microorganism lysis buffer, and a single-use extraction cartridge comprising a chromatography medium for rapid and selective separation of mammalian proteins from microbial proteins. The kit further includes instructions for identification of the microorganism in a fluid by lysing mammalian cells in the bodily fluid; lysing cells of the microorganism: separating proteins of the microorganism from mammalian proteins using the extraction cartridge: and identifying the microorganism by subjecting proteins of the microorganism to mass spectrometry analysis.

Because the methods described herein use a limited set of reagents, the methods of the present invention are suitable for use within a completely automated system for sample preparation and mass spectrometry.

Preferably, the method of the present invention is automated from sample preparation through results reporting. Results may be automatically transferred to a hospital's electronic medical records system where they can be directly linked to patient treatment strategies, insurance, billing, or used in epidemiological reporting. Such an integrated system facilitates epidemiological tracking of an outbreak at the hospital, local, regional, and global levels. For high throughput laboratories, multiple systems can be interfaced to a central computer which integrates data from the different instruments prior to reporting. The system can import phenotypic susceptibility data where it can be combined with identification, virulence, antibiotic resistance and typing information generated by the invention.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 5B shows human alpha-defensins. FIG. 5C shows bacterial proteins. FIG. 5D shows human hemoglobin alpha and beta chains.

FIGS. 8A and 8B illustrate microbial proteins analyzed by ESI-MS. Proteins were eluted from two different SPE-tip materials, Poros R1 (FIG. 8A) and RP-4H (FIG. 8B), and sprayed directly to MS for full scan analysis with m/z range from 600 to 1300.

DETAILED DESCRIPTION

The present invention includes a novel method and system for identification of microorganisms in samples that proteins and other biological material from non-microorganism sources (e.g., proteins of mammalian origin) that can interfere with identification of the microorganisms. Identification of microbes from fluids, tissues, and cultures from patients suspected of having a microbial infection is one of the most critical assays in clinical microbiology and is vital for patient care. Microbes can be identified by mass spectrometry (MS) using intact proteins as analytes, as has been shown using either MALDI-TOF or electrospray ionization (ESI). However, many clinical samples include a very complex and challenging matrix (e.g., mammalian cells, proteins, bodily fluids, media components, etc.) in addition to the target microorganism(s).

The methods and systems described herein include chromatography medium to purify intact proteins prior to mass spectrometry analysis. Proteins from the microbial extract are bound to the chromatography medium, where they are washed and then eluted for mass spectrometry analysis. Surprisingly and unexpectedly, it has been found that the chromatography medium and the methods described herein can rapidly and efficiently remove of a substantial portion of interfering biological material (e.g., mammalian proteins) from a crude cell lysate while preserving high signal strength and removing enough of the interfering protein(s) to allow for identification of the microorganism(s) by mass spectrometry analysis.

Figure 1:
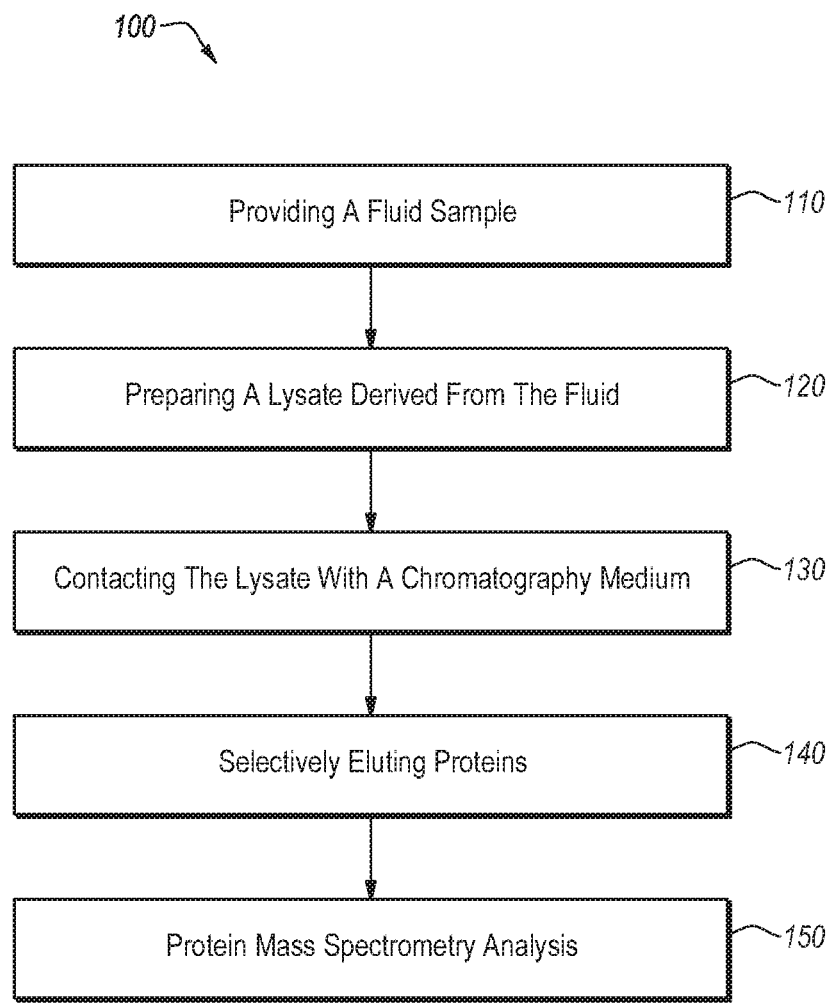
FIG. 1 is a flow diagram illustrating a method for identifying a microorganism.

Referring now to FIG. 1, an overview is provided of a general workflow of a method 100 for rapid extraction and analysis of proteins extracted from a microorganism. The steps of the method 100 may be performed manually using a variety of independent instruments and devices. Alternatively, some or all of the steps may be automated.

In one embodiment, the fluid sample is a fluid (e.g., a bodily fluid) that is suspected of containing an unknown microorganism (e.g., a bacterium, virus, or another infectious agent). The method is applicable to a variety of different sample types, including samples from pure or mixed culture derived from clinical samples including, without limitation, blood, pus, urine, lacrimal fluid, nasal discharge, lymph, synovial fluid, cerebrospinal fluid, stool, sputum, wound and body site swabs, and to samples derived from other sources including industrial or environmental samples such as food (e.g., meat and dairy samples, fruits, and vegetables), beverage, soil, water (e.g., municipal waste water), air, and swabs of surfaces.

Typically, the samples most applicable to the methods and systems described herein are samples with challenging matrices. One example of a sample type with a challenging matrix is a sample that contains highly concentrated foreign or endogenous proteins, ions, lipids, and the like that can suppress or overwhelm the mass spectrometry signal from proteins derived from the unknown microorganism. Examples of common analytical samples with difficult matrices that can interfere with mass spectrometry analysis include, but are not limited to, blood (whole blood or blood culture), urine, and cerebrospinal fluid. In the case of blood, hemoglobin is a significant protein component of blood that spills out of red blood cells when they are lysed. If the hemoglobin is not removed, it can obscure proteins derived from the unknown microorganism. In the case of urine and cerebrospinal fluid, the most likely interfering proteins are defensins. Defensins are small cysteine-rich proteins that function as, host defense peptides. They are active against bacteria, fungi and many enveloped and nonenveloped viruses. They consist of 18-45 amino acids including six (in vertebrates) to eight conserved cysteine residues. Because defensins are involved in defending against microbial infection, it is likely that defensins may be present in urine and cerebrospinal fluid in response to the presence of the microbial agent that the methods and systems described herein are configured to detect.

Referring now to step 120 of the method 100, the method further includes a step of preparing a lysate derived from the fluid sample. The cells in the fluid sample can be lysed by any means known in the art. Typically, any mammalian cells in the sample will first need to be lysed and their contents disposed of. Next, the microbial cells may be washed to removed as much residue as possible from the mammalian cells. And finally, the microbial cells may be lysed.

In one embodiment, the mammalian cells (if present) may be lysed by contacting the fluid sample with a lysing agent selected to lyse mammalian cells in the fluid but not lyse cells of the microorganism. For instance, certain detergents (e.g., nonionic, anionic, cationic, zwitterionic detergents) may be able to effectively lyse mammalian cells. In another instance, the lysing agent may be a saponin. Saponins are plant-derived compounds that are amphipathic glycosides having one or more hydrophilic glycoside moieties combined with a lipophilic triterpene derivative. Saponins have detergent like qualities and, because of their biphasic nature, may be particularly suited to disruption of mammalian cells. In contrast, bacterial cells have rigid cell wall that enables them to be left intact by detergent treatment.

In one embodiment, step 120 may further include separating the cells of the microorganism from the lysed mammalian cells. Separation may, for instance, be accomplished by centrifuging (e.g., at 12,000 g for 2 minutes) the fluid sample to pellet the microbial cells and subsequently disposing of the supernatant. Step 120 may further include washing the cells of the microorganism to wash away proteins derived from the mammalian cells. Washing may be accomplished by, for instance, resuspending the cells of the microorganism in a suitable buffer (e.g., phosphate buffer, TRIS buffer, or the like) and then repelleting them by centrifugation. Washing may be repeated as many times as deemed necessary (e.g., twice).

In one embodiment, step 120 may further include lysing the cells of the microorganism to release the contents thereof. Lysis of the microorganism cells may be accomplished by any means known in the art. Disruption of microorganisms (e.g., bacterial, fungal, *mycoplasma* cells, viruses, and the like) may be achieved by mechanical, chemical, enzymatic and other means as are commonly known in the art. Mechanical approaches include bead beating, use of pressure like French press and the like, sonication, grinding, or other methods known in the art. Chemical methods include exposure to detergents or chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution. In one embodiment, step 120 may further include separating cell fragments and unlysed cells of the microorganism from the contents of the microorganism cells to yield the lysate. In one embodiment, the cells may be resuspended in a small volume for microorganism lysis and cell fragments may be removed by centrifugation. In such a case, the lysate may be obtained by recovering the supernatant. If the lysate is not sufficiently concentrated for mass spectrometry analysis, the lysate may, for example, be concentrated by evaporation at reduced temperature and reduced atmospheric pressure.

In one embodiment, the lysate prepared in step 120 may be contacted with a chromatography medium in step 130. The chromatography medium may be selected to selectively bind either the interfering proteins, the proteins from the at least one microorganism, or both. Likewise, the chromatography medium may be selected to selectively at least partially clean or purify the proteins from the at least one microorganism so that the at least one microorganism can be identified by mass spectrometry (e.g., MALDI or LC/MS). Suitable example of chromatography media include, but are not limited to, reversed-phase or normal phase media, ion exchange media, affinity chromatography media, size exclusion media, hydrophobic interaction media, and combinations thereof.

In one embodiment, contacting the lysate with the chromatography medium includes providing a vessel having therein a selected amount of the chromatography medium, adding the lysate to the vessel and allowing the lysate to mix with the chromatography medium. Alternatively, a selected quantity of the chromatography medium can be added to the tube containing the lysate obtained in step 120 and mixed with the lysate. Further, contacting the lysate with the chromatography medium may include separating the chromatography medium from the lysate. This may typically be accomplished by pelleting the chromatography medium by centrifugation. Such separation could also, for example, be accomplished by filtration. Step 130 may further include washing the chromatography medium at least once with a wash buffer to remove unbound or non-specifically bound material. After washing with the wash buffer, the chromatography medium is separated from the wash buffer. As in the previous example, this may typically be accomplished with centrifugation, or alternatively, filtration or the like.

In another embodiment, contacting the lysate with a chromatography medium may include providing an extraction cartridge that contains a bed of the chromatography medium. The extraction cartridge containing the media may be any extraction cartridge known in the art. In one embodiment, the extraction cartridge is a single-use, disposable cartridge. The extraction cartridge may be loaded, washed, eluted from, etc. manually or the extraction cartridge may include in-line in a liquid chromatography system.

In one embodiment, the extraction cartridge may include a solid phase extraction (SPE) cartridge. In some embodiments, the SPE cartridge may be in line directly with a high resolution/high mass accuracy mass spectrometer. In one embodiment, the SPE cartridge may be a polypropylene tip with a small volume of silica or other sorbent containing bonded $C_4$, $C_8$ or $C_{18}$ or other functional groups immobilized in the cartridge, for example, a StageTip™ cartridge (Thermo Fisher Scientific). In alternative embodiments, polymeric sorbents or chelating agents may be used. The bed volume may be as small as 1 μL or less but greater volumes may also be used. The apparatus and method are well suited to the complex samples derived from the microbial cells because each SPE cartridge is used only once, minimizing carryover problems from one sample to another. A specific embodiment of a solid phase extraction cartridge (e.g., a solid-phase extraction cartridge) is discussed below in reference to FIGS. 2 and 3.

Contacting the lysate with the chromatography medium may further include adding the lysate to the extraction cartridge and allowing the lysate to flow through the bed of chromatography media, and adding a wash buffer to the extraction cartridge and allowing the wash buffer to flow through the bed of chromatography media. The lysate and the wash buffer may be allowed to passively flow through the cartridge or they may be forced through by, for example, centrifugation or positive pressure.

Following contacting the lysate with the chromatography medium, the method 100 may further include a step 140 of selectively eluting the proteins bound to the chromatography medium. The elution protocol used may be dependent to at least some extent on the chemistry of the chromatography medium or the chemistry of the proteins bound to the chromatography medium. In an exemplary embodiment, the chromatography medium is a hydrophobic interaction media (e.g., a reverse phase media) and the elution buffer is an aqueous/organic mixture. For example, the elution buffer may include water and acetonitrile in a range of about 5 vol % acetonitrile to about 75 vol % acetonitrile (e.g., about 10 vol % acetonitrile to about 60 vol % acetonitrile). In one embodiment, the protein(s) may be eluted in at least one fraction. For instance, protein(s) may be eluted at different elution buffer ratios and collected as fractions. In another instance, protein(s) may be eluted isocratically at a selected elution buffer composition ratio and a single fraction may be collected. Likewise, protein(s) may be eluted isocratically at two or more selected elution buffer composition ratios and two or more fractions may be collected.

Following the step 140 of selectively eluting the proteins bound to the chromatography medium, the method may further include a step of subjecting at least one eluted fraction to protein mass spectrometry analysis.

The terms "mass spectrometry" or "MS" as used herein refer to methods of filtering, trapping, detecting, and measuring ions based on their mass-to-charge ratio, or "m/z" (also sometime referred to as "Da/e"). In general, one or more molecules of interest, such as microbial proteins, are ionized and the ions are subsequently introduced into a mass spectrometric instrument where, due to a combination of electric or magnetic and electric fields, the ions follow a path in space that is dependent upon mass ("m" or "Da") and charge ("z" or "e").

The mass spectrometer will include an ion source for ionizing the fraction(s) and creating charged molecules for further analysis. For example ionization of the sample may be performed by matrix-assisted laser desorption ionization (MALDI) or electrospray ionization (ESI). In MALDI, a fraction (or a portion of a fraction) may be combined with a suitable "matrix" (e.g., 3,5-dimethoxy-4-hydroxycinnamic acid (sinapinic acid), α-cyano-4-hydroxycinnamic acid (CHCA, alpha-cyano or alpha-matrix), or 2,5-dihydroxybenzoic acid (DHB)) and spotted onto a plate and dried. Second, a pulsed laser irradiates a spot, triggering ablation and desorption of the sample and matrix material. Finally, the analyte molecules are ionized by being protonated or deprotonated in the hot plume of ablated gases, and can then be accelerated into whichever mass spectrometer is used to analyze the proteins in the spot. In ESI, a stream of liquid droplets are eluted (e.g., from a chromatography system) from a charged cone and gradually desolvated to form protein ions by protonation, deprotonation, water loss, and the like. The ions can then be accelerated into whichever mass spectrometer is used to analyze the proteins. Other ionization techniques include, but are not limited to, atmospheric pressure chemical ionization (ACPI), photo-ionization, electron ionization (EI), chemical ionization (CI), fast atom bombardment (FAB)/liquid secondary ion mass spectrometry (LSIMS), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z) and signal intensity. Suitable analyzers for determining mass-to-charge ratios include quadrupole analyzers, ion trap analyzers, Fourier transform ion cyclotron resonance (FTICR) analyzers, electrostatic trap analyzers, magnetic sector analyzers and time-of-flight analyzers. The ions may be detected by using several detection modes. For example, selected ions may be detected (i.e., using a selective ion monitoring mode (SIM)), or alternatively, ions may be detected using selected reaction monitoring (SRM) or multiple reaction monitoring (MRM) (MRM and SRM are essentially the same experiment.). Ions can also be detected by scanning the mass analyzers to detect all ions from the sample.

In one embodiment, the mass-to-charge ratio may be determined using a quadrupole analyzer. For example, in a "quadrupole" or "quadrupole ion trap" instrument, ions in an oscillating radio frequency (RF) field experience a force proportional to the amplitude of the RF signal, the direct current (DC) potential applied between electrodes, and the ion's m/z ratio. The voltage and amplitude can be selected so that only ions having a particular m/z travel the length of the quadrupole, while all other ions are deflected. Thus, quadrupole instruments can act as a "mass filter," a "mass separator" or an ion lens for the ions injected into the instrument.

One can often enhance the resolution of the MS technique by employing "tandem mass spectrometry" or "MS/MS" for example via use of a triple quadrupole mass spectrometer. In this technique, a first, or parent, or precursor, ion generated from a molecule of interest can be filtered in an MS instrument, and these precursor ions subsequently fragmented to yield one or more second, or product, or fragment, ions that are then analyzed in a second MS procedure. By careful selection of precursor ions, only ions from specific analytes are passed to the fragmentation chamber (e.g., a collision cell), where collision with atoms of an inert gas produce these product ions. Because both the precursor and product ions are produced in a reproducible fashion under a given set of ionization/fragmentation conditions, the MS/MS technique can provide an extremely powerful analytical tool. For example, the combination of ion selection or filtration and subsequent fragmentation can be used to eliminate interfering substances, and can be particularly useful in complex samples, such as biological samples.

In another embodiment, the mass-to-charge ratio may be determined using a hybrid mass spectrometer system containing an electrostatic ion trap mass analyzer capable of high resolution and accurate mass determination, for example a QExactive™ mass spectrometer system (Thermo Fisher Scientific) which contains a quadrupole mass analyzer and an Orbitrap™ mass analyzer. Here, ions are selected by the quadrupole mass analyzer, then passed into a trapping device where the given ion population is collected, collisionally cooled, and injected at high energy and precise trajectory into the Orbitrap mass analyzer. Alternately, precursor ions are selected by the quadrupole mass analyzer, passed to a collision cell where product ions are produced, which are then passed into a trapping device where the given ion population is collected, collisionally cooled, and injected at high energy and precise trajectory into the Orbitrap mass analyzer. Ions oscillate axially across the trap at a frequency proportional to $(z/m)^{1/2}$ where z is the charge on the ion and m is the mass. The image current of these oscillating ions is detected and that frequency domain data is converted into mass spectral information using the principle of Fourier transforms. The longer the transient collection time, the higher the resolution for the subsequent mass spectral data. High resolution data can be obtained at values in excess of 200,000 with mass accuracies of 5 ppm or better.

For example, a flow of liquid solvent from a chromatographic column, possibly containing one or more analytes of interest, enters the heated nebulizer interface of a LC-MS/MS analyzer and the solvent/analyte mixture is converted to vapor. Ions derived from the analytes of interest may be formed in the liquid phase and subsequently ejected into the gas phase by nebulization in the ESI source or by reactions between neutral analytes and reactive ions as the analytes enter the gas phase.

The ions pass through the orifice of the instrument and passes a range of lenses, quadrupole, hexapole and similar devices prior to entering the instrument. In one embodiment, selected m/z windows of any m/z value (e.g., a 3, 5, 10, 20, 30, 40, 50, 100, 1800 or more dalton range of m/z) may be analyzed to determine the molecular weights of the intact proteins in the window(s). In general smaller m/z window sizes may improve signal-to-noise. In addition to the above stated m/z window sizes, the m/z window size may be adjusted dynamically anywhere depending on experimental conditions. In another embodiment, pre-determined ion(s) from the window(s) are allowed to pass into the collision cell where they collide with neutral gas molecules (e.g., argon, nitrogen, or the like) and fragment. The fragment ions generated are passed into the mass analyzer where the fragment ions are separated and forwarded to the detector. In other embodiments, other fragmentation processes may include, but are not limited to, the absorption of infrared photons via infrared multiple photon dissociation (IRMPD), the absorption of a single UV photon, through ion-ion reactions including electron transfer dissociation (ETD), or collisional-activation of electron transfer product ions which do not undergo prompt fragmentation, electron capture dissociation (ECD). In an exemplary embodiment, the dissociation method is the high energy collision-induced dissociation (HCD). As ions collide with the detector they produce analog signal which is further converted to a digital signal.

The acquired data is relayed to a computer, which plots voltage versus time. The resulting mass chromatograms are similar to chromatograms generated in traditional HPLC methods. Concentrations of the analytes of interest may be determined by calculating the area under the peaks in the chromatogram, if there are any chromatographic peaks, or using the intensity of peaks in mass spectrum. The concentration of the analyte or analytes of interest (e.g., proteins) in the sample is accomplished via one of many different techniques known in the state of the art involving external or internal calibrations, relative quantitation, peak height or area counts, standard addition, or any other method known in the state of the art.

Figure 2:
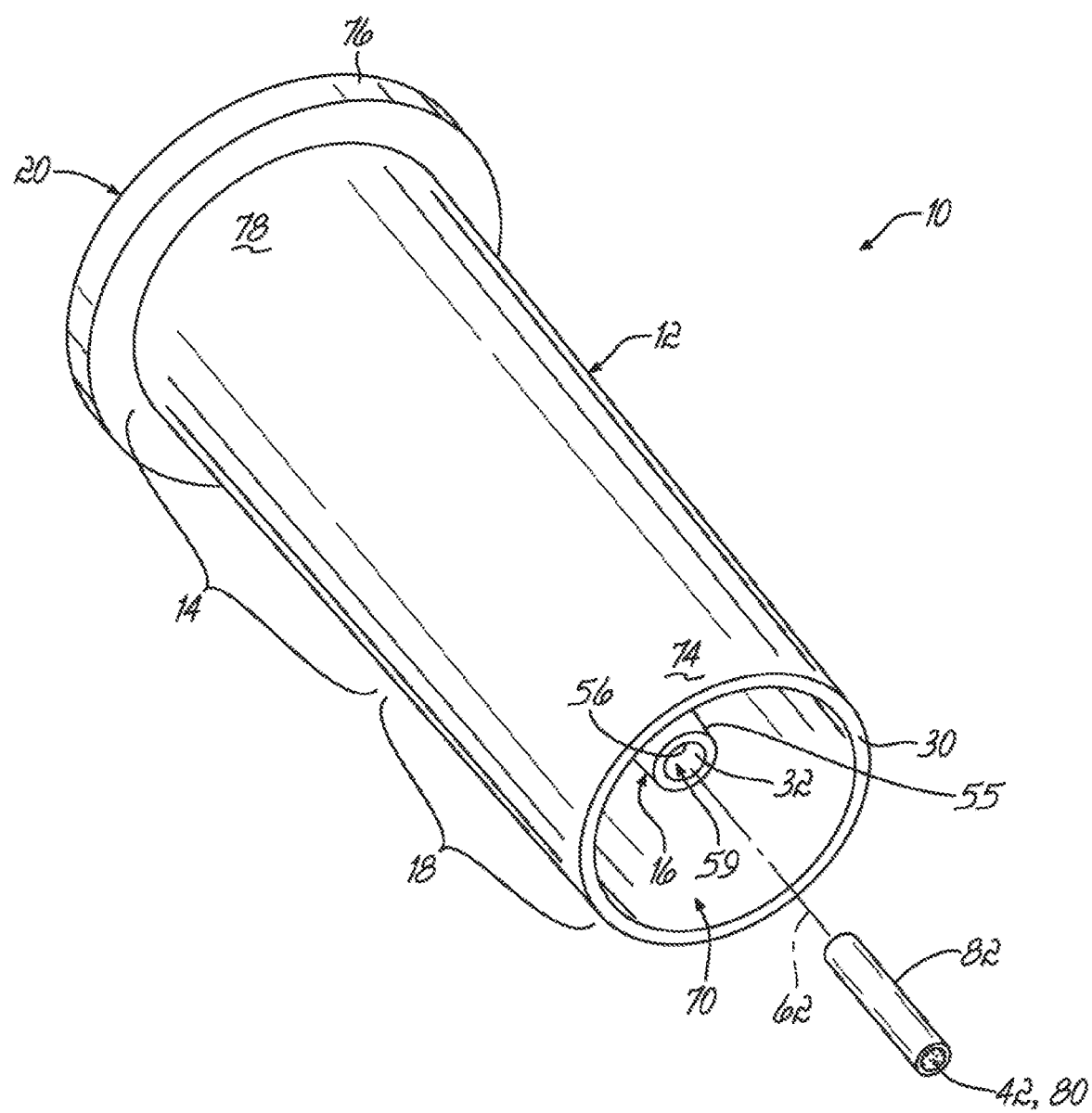
FIG. 2 is a disassembled perspective view of an extraction cartridge in accordance with embodiments of the invention.
Figure 3:
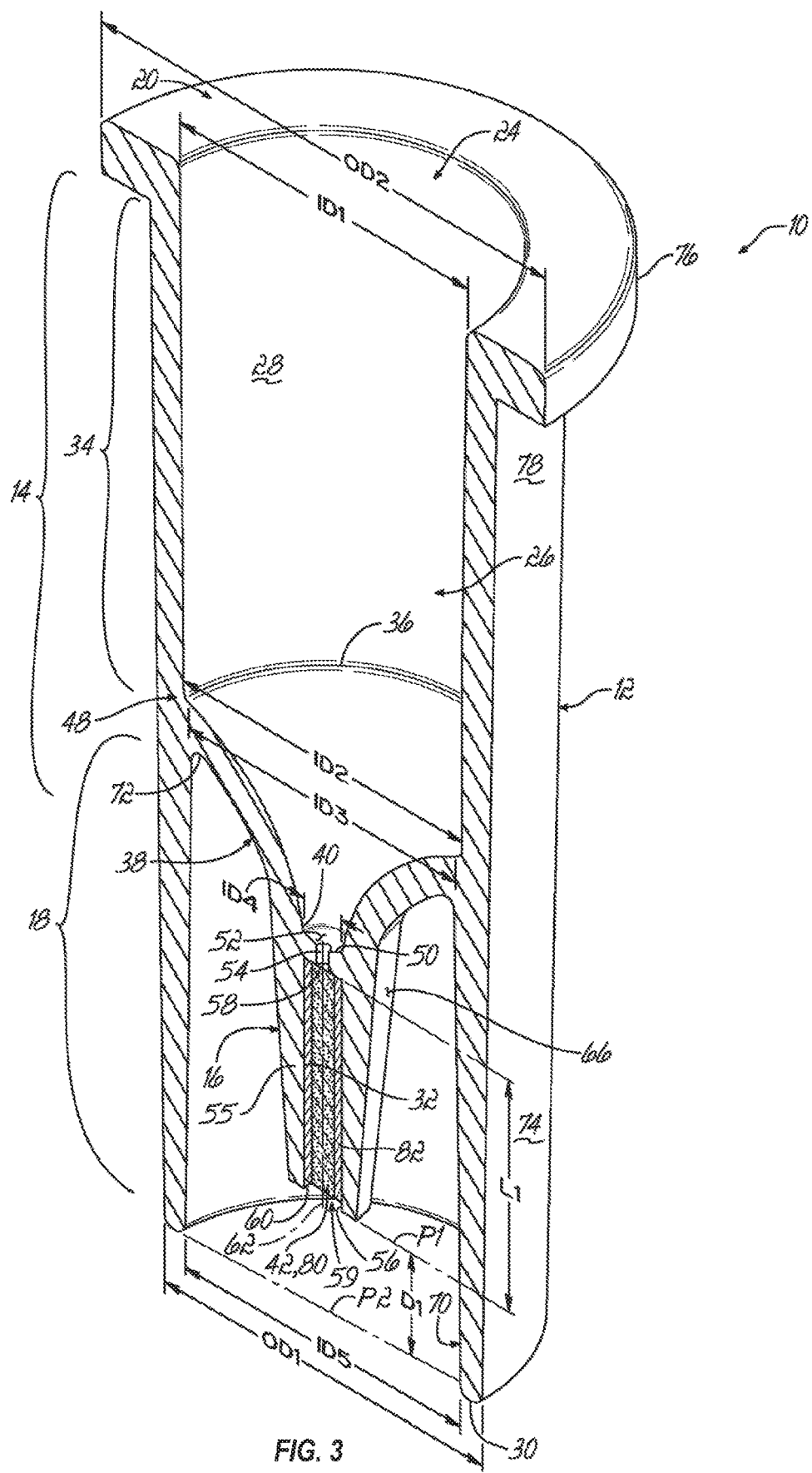
FIG. 3 is a perspective view in longitudinal cross-section of the extraction cartridge of FIG. 2 in an assembled state.

With reference to FIGS. 2 and 3, an embodiment of an extraction cartridge 10 (e.g., a single use extraction cartridge) that may be employed in the method described above is illustrated. The illustrated extraction cartridge 10 may be used for extracting a component, such as protein or protein fragment, from a sample containing a mixture of components such as proteins, peptides, carbohydrates, lipids, nucleic acids, salts, and small molecules. The extraction cartridge 10 includes a cartridge body 12 having a reservoir portion 14, an extraction media portion 16, and a collar 18.

The reservoir portion 14 is generally located at the proximal end 20 of the cartridge body 12 and includes an inlet 24 and a cavity that functions as a reservoir 26. The reservoir 26 is defined by the inner surface 28 of the reservoir portion 14 and is in fluid communication with the cavity 32 of the extraction media portion 16, which is generally located at the distal end 30 of the cartridge body 12. The reservoir 26 is capable of holding a volume of liquid. In an embodiment, the volume of the reservoir 26 is sufficient to hold the volume of liquid needed to prime the extraction medium 42, the volume of the sample to be extracted, the volume of the wash solutions, and the volume of the elution solution. For example, in some extraction methods, it is necessary to dilute a sample with a suitable solvent before forcing the sample through the extraction medium 42 located in the cavity 32 of the extraction media portion 16. Typically, the step of diluting the sample is performed in a separate vessel. In the exemplary embodiment, the volume of the reservoir 26 is sufficient to dilute the sample directly in the reservoir 26 before positive pressure is applied to the reservoir 26 to transfer the sample to the extraction medium. In an embodiment of the invention, the reservoir 26 has a volume ranging from about 50 μl to about 1500 μl.

In the exemplary embodiment illustrated in FIGS. 2 and 3, the inner surface 28 of the reservoir 26 includes a first portion 34 proximal the inlet 24 that provides a majority of the volume of the reservoir 26 and a second portion 38 proximal the extraction media portion 16. In the exemplary embodiment illustrated in FIGS. 2 and 3, the inner surface 28 of first portion 34 of the reservoir 26 is generally frustoconical-shaped and has an angle of convergence between the inner diameter ID1 at the proximal end of the first portion 34 and the inner diameter ID2 at the distal end 36 of the first portion 34 that is less than about 10 degrees or, in an alternative embodiment, less than 4 degrees. As used herein, the angle of convergence is the angle between the surface referred to and the central axis of the structure, which, in the present instance, is the central axis 62 of the cartridge body 12.

In one embodiment, the reservoir 26 may have a shape configured to be sealed against a liquid handling device (e.g., a micropipette or a liquid chromatography system) that can create positive air pressure in the reservoir 26 to force liquid in the reservoir 26 through the extraction medium 42. In a related embodiment, the extraction media portion 16 and/or the collar 18 may have a shape configured to a liquid receiver configured to receive liquids (e.g., an eluate) flowing out of the extraction media portion 16. Likewise, the extraction media portion 16 may be sized and shaped to be coupled to a liquid handling device (e.g., a liquid chromatography system) configured to receive downstream flow from the extraction media portion 16.

The second portion 38 of the reservoir 26 may be funnel-shaped and have an annular wall that tapers inwardly toward the extraction media portion 16, as illustrated in FIG. 3. The second portion 38 of the reservoir 26 has an angle of convergence between the inner diameter ID3 at the proximal end 48 of the second portion 38 and the inner diameter ID4 at the distal end 50 of second portion 38. In the exemplary embodiment, the angle of convergence of the first portion 34 of the reservoir is less than the angle of convergence of the second portion 38 of the reservoir 26.

In the embodiment exemplified in FIG. 3, the second portion 38 of the reservoir 26 includes a shelf 52 that further reduces the diameter of the reservoir 26 as it transitions into the fluid passageway 54 between the reservoir 26 and the cavity 32 of the extraction media portion 16. The shelf 52 may function as a sealing surface to form a seal with a liquid delivery device, such as a pipette tip or a hollow probe like a hollow ceramic probe. The shelf 52 in the exemplary embodiment of FIG. 3 is illustrated as having a generally frustoconical shape with an obtuse angle of convergence in a range from about 45 degrees to about 90 degrees.

The embodiment illustrated in FIG. 3 includes a fluid passageway 54 between the reservoir 26 and the cavity 32 of the extraction media portion 16. In this exemplary embodiment, the fluid passageway 54 is frustoconical-shaped and the angle of convergence is typically less than about 10 degrees, and in an alternative embodiment, is less than about 1 degree. The fluid passageway 54 has a length and internal diameter that minimizes the volume of the fluid passageway 54 while at the same time provides sufficient flow to prevent a buildup of backpressure caused by a restricting flow through the fluid passageway 54. The volume of the fluid passageway 54 is minimized to minimize the dead volume in the extraction cartridge. In an embodiment, the volume of the fluid passageway 54 does not exceed about 1000 nl and may be in a range from about 1 nl to about 50 nl.

The extraction media portion 16 includes an elongated sleeve 55 having an inner surface 56 defining a cavity 32 with an extraction medium 42 disposed therein. The cavity 32 includes an inlet end 58 in fluid communication with the reservoir 26 and an outlet end 60 having an opening 59 disposed remote from the inlet end 58. In an embodiment, the cavity 32 is frustoconical-shaped with an angle of convergence of less than about 5 degrees, and in an alternative embodiment, the angle of convergence may range from about 0.2 degrees to 1 degrees. In another alternative embodiment, the angle of convergence of the frustoconical-shaped cavity 32 may be about 0.4 degrees. In embodiments having a frustoconical-shaped cavity 32, the larger diameter end of the cavity 32 opens toward the insertion point for the extraction medium 42. The internal diameter of the cavity 32 for the alternative embodiment also ranges from about 0.5 mm to about 2.0 mm, and preferably from about 0.75 mm to about 0.85 mm. The cartridge body 12 has a central axis 62 that extends through the cavity 32 of the extraction media portion 16. The cavity 32 has a length L1 along the central axis 62 between the inlet end 58 and the outlet end 60. In an embodiment, the length L of the cavity 32 is in a range from about 1 mm to 10 mm. In another embodiment, the length L1 of the cavity 32 is in a range from about 3 mm to about 5 mm and is preferably in a range from about 3.5 mm to about 4.5 mm. In an embodiment, the length L1 of the cavity corresponds with the length of the elongated sleeve 55.

The collar 18 of the cartridge body 12 extends axially in a common direction with the elongated sleeve 55. In the embodiment illustrated in FIGS. 2 and 3, the collar 18 has a closed end 72 that is coupled to the external surface 78 of the reservoir portion 14 adjacent the transition between the first and second portions 34, 38. In the illustrated embodiment, the external surface 74 of the collar 18 is continuous with the external surface 78 of the reservoir portion 14. The external surfaces 78, 74 of the reservoir portion 14 and the collar 18 may be tapered with an angle of convergence of less than 15 degrees, and in an alternative embodiment, in a range from about 0.1 degree to about 5 degrees.

The collar 18 has an open terminal end 70 that is spaced apart from the outlet end 60 of the elongated sleeve 55. The outlet end 60 of the elongated sleeve 55 defines a plane P1. The terminal end 70 of the collar 18 defines a plane P2 that extends at least to the plane P1 defined by the outlet end 60 of the elongated sleeve 55. In an embodiment, the plane P2 of the terminal end 70 of the collar 18 extends beyond plane P1 of the outlet end 60 of the elongated sleeve 55. In the embodiment illustrated in FIGS. 2 and 3, the plane P2 of the terminal end 70 of the collar 18 extends beyond plane P1 of the outlet end 60 of the elongated sleeve 55 by a distance D1 sufficient to prevent contact of the outlet end 60 of the elongated sleeve 55 by any portion of a second extraction cartridge. For example, the distance D1 may range from about 0.1 mm to about 2 mm, which, depending on the inner diameter ID5 at the terminal end 70 of the collar 18 and the smaller of the outer diameter OD1 at the terminal end 70 of the collar 18 or the outer diameter OD2 at the proximal end 20 of the cartridge body 12, may be sufficient to prevent contact of the outlet end 60 of the elongated sleeve 55 by any portion of a second extraction cartridge. This structure prevents the damage to the outlet end 60 of the elongated sleeve 55 when the extraction cartridges 10 are loosely stored in a bag or box. An additional benefit of the plane P2 extending beyond plane P1 is that it prevents contamination of the outlet end 60 of the elongated sleeve 55 when the extraction cartridge 10 is being handled by an automated sample analysis system. For example, a method of transporting extraction cartridges 10 in automated analysis systems is to have the extraction cartridge 10 drop through a guiding pipe or hose from one location in the system to another location. If the outlet end 60 of the elongated sleeve 55 is exposed, i.e., not protected by a collar 18, there is a significant risk of carryover contamination of the outlet end 60 if the outlet end 60 contacts the surfaces of the transporting pipe or hose. 1o The collar 18 of the present invention protects the outlet end 60 of the elongated sleeve from contacting the surfaces of the transporting hose and thereby diminishes the risk of carryover contamination between different extraction cartridges transported in the same hose.

The terminal end 70 of the collar 18 has an outer diameter OD1 and the inlet 24 of the reservoir 26 has an inner diameter ID1 such that the terminal end 70 of the collar 18 may not be fully inserted into the inlet 24 of the reservoir 26. In an embodiment, the inner diameter ID1 of the inlet 24 of the reservoir is not greater than the outer diameter OD1 of the terminal end 70 of the collar 18. In another embodiment, the inner diameter ID1 of the inlet 24 of the reservoir is less than the outer diameter OD1 of the terminal end 70 of the collar 18. Similarly, the proximal end 20 of the cartridge body 12 has an outer diameter OD2 and the open terminal end 70 of the collar 18 has an inner diameter ID5 such that the proximal end 20 of the cartridge body 12 may not be fully inserted into the open terminal end 70 of the collar 18. In the embodiment illustrated in FIGS. 2 and 3, the outer diameter OD2 at the proximal end 20 of the cartridge body 12 includes an optional shoulder 76. In an embodiment, the inner diameter ID5 of the open terminal end 70 of the collar 18 is not greater than the outer diameter OD2 of the proximal end 20 of the cartridge body 12. In another embodiment, the inner diameter ID5 of the open terminal end 70 of the collar 18 is less than the outer diameter OD2 of the proximal end 20 of the cartridge body 12. When multiple extraction cartridges 10 are stored together with random packaging, such as in a bag or box, the extraction cartridges 10 will not stack one inside the other as would happen if one end of the extraction cartridge were capable of fitting inside an opening in an end of a second extraction cartridge. This aspect of the extraction cartridges 10 makes it significantly easier for an automated system to pick up one extraction cartridge 10 at a time and allows the extraction cartridges 10 to be utilized with automated systems without being sorted and placed into racks. Therefore the extraction cartridges 10 can be packed, sold, stored and inserted to the an automated analytical system in loose batches without the need to pack them in specified positions and specified orientation in a rack or tray thereby improving efficiency and saving money, space and labor.

In the embodiment illustrated in FIGS. 2 and 3, the proximal end 20 of the cartridge body 12 includes an optional shoulder 76 projecting outwardly from the external surface 74 of the reservoir portion 14 adjacent the inlet 24. The shoulder 76 increases the outer diameter of the proximal end 20 of the cartridge body 12 and provides a surface that may be used as by automated devices to hang the extraction cartridge 10 during handling or if it is desired to hang the extractions cartridge 10 in a tray or rack system.

The extraction medium 42 is disposed in the cavity 32 of the extraction media portion 16. The extraction medium 42 allows for the extraction of a desired component from a mixed sample. The extraction medium 42 may chromatographically separate proteins from other components in a mixed biological sample. Embodiments of the extraction medium 42 are capable of reversibly binding small molecules or macromolecules such as peptides and proteins having a molecular weight that range from about 1 kDa to about 200 kDa. The extraction medium 42 may be capable of reversibly binding at least 1 µg of protein in a sample volume that ranges from about 10 µl to about 100 ml when the sample is passed through the extraction medium 42 at a flow rate in the range of about 50 µl/min to 200 µl/min. The extraction medium 42 may also elute the desired component based on a desired characteristic such as the molecular weight of the component, hydrophobicity, charge, or the affinity of the component for an aspect of the extraction medium 42. In an embodiment, the extraction medium 42 is capable of eluting at least 20% of the proteins bound from the mixed sample when eluted at a flow rate ranging from about 0.1 µl/min to about 20 µl/min with a volume of elution solvent ranging from about 1 µl to about 100 µl.

In an embodiment, the extraction medium 42 is a solid phase extraction medium and, more particularly, a porous monolith medium 80 having high internal porosity that allows sufficient flow of a sample through the porous monolith medium 80 without generating undesirable high backpressures. In an embodiment, the backpressure does not exceed about 5 bar at a flow rate of 200 µl/min. The porous monolith medium 80 is preferably capable of withstanding at least 200 bar. A benefit of the pore structure of the porous monolith medium 80 is that it results in a tortuous path for the sample that allows for rapid convective mass transfer at fast flow rates. Also, a porous monolith medium 80 does not require a frit to retain its position within the cartridge body 12.

The porous monolith medium 80 may be prepared as a continuous bed inside of a sheath, such as a section of tubing 82. The result is that upon cutting the tubing 82 into sections, the porous monolith medium 80 is present in the full length of a microcolumn that functions as the extraction medium 42.

In the embodiment illustrated in FIGS. 2 and 3, the extraction medium 42 is a porous monolith medium 80 that is inserted into the cavity 32 of the extraction media portion 16 of the cartridge body 12 from the outlet end 60 of the elongated sleeve 55 of the extraction media portion 16. A benefit of preparing the porous monolith medium 80 inside tubing 82 and cutting the tubing 82 to form a microcolumn is that this method avoids the formation of a semi permeable or non porous layer at the boundary between the air and the polymerizing porous monolith medium, such as occurs when the porous monolith medium is allowed to polymerize directly inside of a pipette tip. The semi permeable or non porous layer can adversely affect the flow characteristics of the resulting porous monolith medium. In embodiments in which the porous monolith medium is formed directly inside the cavity 32 of the extraction media portion 16, the adverse effects of the semi permeable or non-porous layer may be decreased by forming a passageway through the center of the porous monolith medium to increase the flow rate of the sample through the extraction medium. However, a high proportion of the component to be captured may remain in the passageway and bypass the porous monolith medium thereby requiring multiple passes of the sample through the medium for maximum extraction. In contrast, preparing the porous monolith medium 80 inside tubing 82 which is cut into segments produces a porous cylinder where the pore structure and porosity is uniform across the diameter and along the length of the porous monolith medium 80. This preparation process results in the flow of a sample through the porous monolith medium 80 unhindered by semi permeable or non porous surfaces and results in substantially uniform binding across the porous monolith medium 80 to provide maximal extraction of the desired component in a single pass through the porous monolith medium 80.

Tubing 82 on the outside of the porous monolith medium 80 provides a protective layer that aids with handling the porous monolith medium 80. For example, during the manufacture of the extraction cartridge 10, the cartridge body 12 may be formed independently of the porous monolith medium 80. The porous monolith medium 80 is then inserted into the cavity 32 of the extraction media portion 16 of the cartridge body 12. In embodiments in which the porous monolith medium 80 formed in a section of tubing 82, the tubing 82 allows the porous monolith medium 80 to be more easily handled for insertion into the cavity 32 of the extraction media portion 16. In addition, when the porous monolith medium 80 is inserted into the cavity 32 of the reservoir portion 14, the wall of the tubing 82 may act as a support for the porous monolith medium 80 and may act as a sealing surface against the inner surface 56 of the cavity 32 to prevent back flow around the porous monolith medium 80.

When the porous monolith medium 80 formed in a section of tubing 82 is inserted into the cavity 32 of the extraction media portion 16, the tubing 82 compresses around the porous monolith medium 80 to prevent the porous monolith medium 80 from being extruded from the tubing 82.

The porous monolith medium 80 may optionally be coupled to the inner surface of the tubing 82 to improve resistance to extrusion of the porous monolith medium 80. For example, the inner surface of the tubing 82 may be treated to create covalent bond attachment points for the polymerizing porous monolith medium 80. To activate the inner surface of a tubing such as polyethylene ether ketone (PEEK) tubing, the interior of the tubing may be filled with reaction solution containing a solvent such as acetonitrile or propionitrile (alkyl nitrile derivatives) and an azo-class initiator such as Vazo-64 or Vazo-55 in a concentration from about 1% to about 10% (volume). The filled tubing may then be heated to a minimum of 80% of the solvent's 10-hour half life temperature, for example Vazo-64 has a 10-hour decomposition half life at 64 degrees Celsius. The reaction may be allowed to proceed for at least 30 minutes. The reaction solution may be replaced with fresh reaction solution and allowed to proceed for an additional duration of at least 30 minutes. In an embodiment, the ends of the tubing are sealed generating an internal backpressure of at least 5 psi. In another embodiment, the reaction solution is continuously replenished at ambient pressure. The reaction solution is then removed from the tubing and the tubing is allowed to dry with a stream of nitrogen. After drying, the polymerization mixture is injected into the lumen of the activated tubing. During polymerization of the porous monolith medium 80, the activated attachment points on the inner surface of the tubing are incorporated into the extraction medium.

While PEEK tubing is used as the exemplary tubing, other types of polymeric tubing may be used including cyclic olefin copolymers ("COC") and fluoro-polymers such as ethylene tetrafluoroethylene (ETFE), fluorinated ethylene propylene (FEP) and other fluoro-polymers. Additionally, fused silica tubing may be used and is activated by covalently binding an acrylate- or methacrylate-containing silanization reagent after hydrolysis of the fused silica.

The tubing 82 may have an inner diameter that ranges from about 0.1 mm to about 1 mm. In an embodiment, the inner diameter of the tubing 82 ranges from about 0.4 mm to about 0.6 mm. In another embodiment, the inner diameter of the tubing is about 0.5 mm. The tubing 82 with porous media formed inside may be cut to a length that, when combined with the inner diameter of the tubing, provides the desired volume for the porous extraction media. In an embodiment, the length of the tubing 82 with porous monolith medium 80 is cut into sections ranging from about 6 mm to about 2 mm and in an alternative embodiment, the length ranges from about 3 mm to about 5 mm or is about 4 mm. After the porous extraction medium polymerizes, the tubing may be cut to the desired length with a tubing cutter such as an IDEX A-350 tubing cutter.

The porous monolith medium 80 may be prepared by polymerization of a mixture that includes suitable monomers and/or polymers in the presence of an initiator and a pore-forming solvent (porogen). The resulting porous monolith medium 80 has pores ranging in diameter from about 50 nm to about 20,000 nm. The porous monolith medium 80 may have pores in the range of about 50 nm-200 nm or about 750-10,000 nm. The porous monolith medium 80 may be polymer globules having a diameter that ranges from about 20 nm to about 10,000 nm. The porous monolith medium 80 should be capable of withstanding at least about 200 bar pressure.

The monomers may be selected from vinyl containing monomers, acrylate containing monomers, methacrylate containing monomers, acrylamide, fluoro-substituted ethylene, and combinations thereof. Polymers may be selected from polyolefin, polyester, polyurethane, polyamide, and combinations thereof. The vinyl containing monomers may include vinyl aromatic monomers such as monovinyl substituted aromatic monomers and divinyl substituted aromatic monomers and combinations thereof. Exemplary vinyl aromatic monomers include divinyl benzene, styrene, alkyl substituted styrene such as ethyl vinyl benzene, alpha-methylstyrene, alkyl substituted alpha-methyl styrene, halogen substituted alpha-methyl styrene such as chloromethyl styrene and combinations thereof. The alkyl substitutions may include up to 18 carbon atoms. The acrylate containing monomers include mono-, di-, and tri-acrylates. The methacrylate monomers include mono-, di-, and tri-methacrylates such as glycidyl methacrylate, ethylene dimethacrylate, trimethylolpropane, trimethylacrylate, hydroxyethyl methacrylate. In an embodiment, the monomers, or mixtures of at least two monomers, or mixtures of at least one monomer and one polymer, are generally present in the polymerization mixture in an amount of from about 10 vol. % to about 60 vol. %, and in an alternative embodiment, in an amount of from about 20 vol. % to about 70 vol. %.

The porogen may be selected from a variety of different types of materials. For example, suitable liquid porogens include aliphatic hydrocarbons, aromatic hydrocarbons, esters, alcohols, ketones, ethers, solutions of soluble polymers, and mixtures thereof. Exemplary porogens include 4,4,4-trimethyl pentane, alcohols having from 1 to 12 carbon atoms, toluene, butylacetate, 1,4, butanediol, water, acetone, hexane, cyclohexane, cyclohexanol, tetrahydrofuran (THF) and combinations thereof. In an embodiment, the porogen is generally present in the polymerization mixture in an amount of from about 20 vol. % to about 90 vol %, and in an alternative embodiment, from about 60 vol. % to about 80 vol °%.

The initiators may include thermal polymerization initiators, conventional free-radical polymerization initiators, photoinitiators, and redox initiators. Examples of suitable initiators include peroxides such as OO-t-amyl-O-(2ethylhexyl)monoperoxycarbonate, dipropylperoxydicarbonate, and benzoyl peroxide, azo compounds such as azobisisobutyronitrile (Dupont Vazo-64), 2,2'-azobis(2-amidinopropane)dihydrochloride, and 2,2'-azobis(isobutyramide)dihydrate, and ammonium persulfate and tetramethylethylenediamine (TMEDA). In an embodiment, the initiator is generally present in the polymerization mixture in an amount of from about 0.2% by weight to about 5% by weight of the monomers and in an alternative embodiment, from about 1% by weight to about 2% by weight of the monomers.

The components of the polymerization mixture may be mixed in accordance with routine techniques and injected into the interior of the tubing and allowed to polymerize. For example, in an embodiment, the tubing is filled with the polymerization mixture and pressured is applied to about 100 psi. Pressurization helps prevent the formation of bubbles in the polymerization mixture as nitrogen is formed during the decomposition of the initiator during polymerization. In other embodiments, the tubing is filled with the polymerization mixture and both ends of the tubing are sealed while polymerization is allowed to proceed. Sealing both ends of the tubing results in increased pressure in the interior of the tubing as polymerization proceeds, which prevents the formation of nitrogen bubbles. In yet another embodiment, the tubing is filled with the polymerization mixture and one end of the tubing is sealed and the other end of the tubing is left open but placed in vial. The filled tubing is heated during the polymerization step. Locating the open end of the tubing in a vial allows for liquid expansion while the mixture is heated during polymerization, which prevents pressure increases caused by heating that could detrimentally affect the porosity of the porous monolith medium. In embodiments utilizing a photoinitiator, the filled tubing may be subjected to UV irradiation. Examples of porous monolith media and methods of making the same are described in U.S. Pat. No. 7,922,908, which is incorporated by reference in its entirety.

The porous monolith medium 80 may also be functionalized. For example, the porous monolith medium 80 may be prepared where the epoxide or halide functionality can be reacted with amines or sulfides to create, for example, anion exchange media or with, for example carboxylic acid, phosphoric acid, sulfonic acid to create cation exchange media. These groups may then be further modified to allow attachment of proteins, peptides or immunoglobulins to create affinity separation and extraction media. Epoxide groups may be either reacted directly with proteins, peptides or immunoglobulins or after conversion to aldehyde. Other affinity media that are possible include immobilized metal ion affinity chromatography (IMAC) phases and boronate phases.

Exemplary porous materials suitable for use as the porous monolith medium 80 and the methods of making such materials are described in U.S. Pat. Nos. 5,334,310 and 5,633,290, each of which is incorporated by reference in its entirety.

In an alternative embodiment, the extraction medium 42 may include a plurality of porous and/or non-porous beads, such as glass, silica or polymeric beads, that are contained in the cavity 32 of the extraction media portion 16. In this embodiment, the inlet end of the cavity may include a first frit and the outlet end of the cavity may include a second flit. The flits function to prevent the beads from escaping the cavity. The beads are packed into the cavity sufficient to allow for a sufficient flow rate while not creating undesirable backpressure. Exemplary beads are described in U.S. Pat. No. 6,783,672, which is incorporated by reference in its entirety.

During use, before a sample is passed through the extraction cartridge 10, the extraction medium 42 may be wetted with a wetting solvent. In embodiments wherein the extraction medium 42 includes a porous monolith medium 80, the porous monolith medium 80 may be wetted with a sufficient volume of a wetting solvent that may include an organic solvent such as acetonitrile (ACN) and an aqueous component such as water with 0.2 vol. % formic acid (FA). Typically about 10 µl to about 100 µl of wetting solvent may be used to wet the porous monolith medium 80. The porous monolith medium 80 may then be equilibrated with an equilibration solvent that may include water and about 0.2 vol. % FA. Typically about 10 µl to about 100 µl of equilibration solvent may be used to equilibrate the porous monolith medium 80. Samples containing compounds of interest, such as proteins, in volumes ranging from 10 µl to 100 µl are then forced through the porous monolith medium 80 in the extraction cartridge 10. The flow through from the samples may optionally be collected for additional analysis. The porous monolith medium 80 may then be washed with a wash solution that includes water and about 0.1 vol. % to about 0.2 vol. % FA. Typically about 10 µl to about 100 µl of wash solution may be used to wash the sample captured in the porous monolith medium 80. The compounds captured by the porous monolith medium 80 are then eluted with an elution solution. The content of the elution solution and the volumes and elution times may vary depending on the type of elution that is desired. Where quick elution is desired, the elution solution may include water, an organic component in a range of about 20-60 vol. %, and about 0.2 vol. % FA; about 1 µl to about 100 µl of elution solution is used to elute the capture compounds from the porous monolith medium 80. The liquid solutions, including the sample, may be rapidly pushed through the extraction medium 42. Compound binding in the extraction medium 42 occurs rapidly and the elution time is dependent on the desired application. Isocratic elution or elution using fast gradients enables extremely fast performance that can be used with automated systems in circumstances where high throughput is desired. When used in combination with high-resolution mass spectrometry, it is possible to identify compounds such as proteins using fast elution. Such methods may be useful where rapid analysis is needed such as microbial identification. When more detailed analysis is desired, the elution may be performed slowly allowing the compounds to elute sequentially from the extraction cartridge 10 according to a desired characteristic, such as molecular weight, charge, hydrophobic interaction, or other affinity-type interaction with components of the extraction cartridge 10. The slow elution can be done with a short (e.g., about 5 minutes) or long (e.g., about 30 minutes) elution gradient. For example, in an embodiment, the percentage of organic component in the elution solvent may be increased continuously or stepwise throughout the gradient to allow for elution over a desired duration. The longer elution durations enable analysis of a single targeted compound, such as an antibiotic resistance marker in a microbial sample or a cancer biomarker from a biopsy. The possibility of applying a gradient for effective compound separation allows the user to avoid having to use an expensive and time consuming analytical cartridge. Analytical columns are used multiple times requiring wash steps to avoid carryover from one sample to another. The present extraction cartridge 10 may be disposable and enable the user to avoid washing steps and carryover from one sample to the next.

The eluted compounds may be collected for later analysis, passed directly into an analysis system (e.g., an LC-MS system), or mixed with a matrix and spotted for MALDI analysis.

Additional discussion of the extraction cartridge 10 presented above can be found in U.S. patent application Ser. No. 14/735,900, which is incorporated herein in its entirety.

Example 1

Described below is a method for identifying a microorganism that may use an extraction cartridge (e.g., a single-use extraction cartridge) like the one described above. The microorganism (e.g., an infectious agent) may be in a fluid that includes interfering mammalian proteins and proteins from the microorganism.

In an initial step, the method includes preparing a lysate from the fluid (e.g., blood, blood culture, cerebrospinal fluid, or urine) that includes the mammalian proteins and the proteins from the microorganism. In one embodiment, the lysate may be prepared by (a) lysing mammalian cells, if present in the fluid, by contacting the mammalian cells with a lysing agent (e.g., a natural or synthetic detergent) selected to lyse the mammalian cells but not cells of the microorganism, (b) separating the cells of the microorganism from the lysed mammalian cells, (c) washing the cells of the microorganism, (d) lysing the cells of the microorganism to release the contents thereof, and (e) separating unlysed microorganism cells and cell fragments from the contents of the microorganism cells to yield the lysate.

The method further includes separating proteins derived from the microorganism from the mammalian proteins. The separating includes (a) providing a single use extraction cartridge that contains a bed of a chromatography medium, (b) adding the lysate to the extraction cartridge and allowing the lysate to flow through the bed of chromatography media, (c) washing the extraction cartridge with a wash buffer; and (d) selectively eluting proteins bound to the chromatography medium to produce at least one eluted fraction. In one embodiment, the selectively eluting may include flowing through the bed of chromatography medium different concentrations of an aqueous elution buffer that includes a polar organic solvent (e.g., acetonitrile) in a concentration range of 10 vol % to 60 vol %. The method further includes subjecting the at least one eluted fraction to protein mass spectrometry analysis to identify the presence of one or more infectious agent in the blood sample. Suitable example of mass spectrometry analysis techniques include, but are not limited to, MALDI-TOF, ESI-MS, or ESI-MS$^n$ (e.g., MS/MS).

The method described herein is applicable to many types of microorganisms and types of matrices. In one embodiment, the microorganism is one or more of a Gram positive bacteria, Gram negative bacteria, archea, mycobacteria, *mycoplasma*, yeasts, viruses, and filamentous fungi.

In one embodiment, the mammalian cells (if present) may be lysed by contacting the fluid sample with a lysing agent selected to lyse mammalian cells in the fluid but not lyse cells of the microorganism. For instance, certain detergents (e.g., nonionic, anionic, cationic, zwitterionic detergents) may be able to effectively lyse mammalian cells. In another instance, the lysing agent may be a saponin. Saponins are plant-derived compounds that are amphipathic glycosides having one or more hydrophilic glycoside moieties combined with a lipophilic triterpene derivative. Saponins have detergent like qualities and, because of their biphasic nature, may be particularly suited to disruption of mammalian cells. In contrast, bacterial cells have rigid cell wall that enables them to be left intact by detergent treatment.

In one embodiment, the method may further include separating the cells of the microorganism from the lysed mammalian cells. Separation may, for instance, be accomplished by centrifuging (e.g., at 12,000 g for 2 minutes) the fluid sample to pellet the microbial cells and subsequently disposing of the supernatant. The method may further include washing the cells of the microorganism to wash away proteins derived from the mammalian cells. Washing may be accomplished by, for instance, resuspending the cells of the microorganism in a suitable buffer (e.g., phosphate buffer, TRIS buffer, or the like) and then repelleting them by centrifugation. Washing may be repeated as many times as deemed necessary (e.g., twice).

In one embodiment, the method may further include lysing the cells of the microorganism to release the contents thereof. Lysis of the microorganism cells may be accomplished by any means known in the art. Disruption of microorganisms (e.g., bacterial, fungal, *mycoplasma* cells, viruses, and the like) may be achieved by mechanical, chemical, enzymatic and other means as are commonly known in the art. Mechanical approaches include bead beating, use of pressure like French press and the like, sonication, grinding, or other methods known in the art. Chemical methods include exposure to detergents or chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution. In one embodiment, the method may further include separating cell fragments and unlysed cells of the microorganism from the contents of the microorganism cells to yield the lysate. In one embodiment, the cells may be resuspended in a small volume for microorganism lysis and cell fragments may be removed by centrifugation. In such a case, the lysate may be obtained by recovering the supernatant. If the lysate is not sufficiently concentrated for mass spectrometry analysis, the lysate may, for example, be concentrated by evaporation at reduced temperature and reduced atmospheric pressure.

In one embodiment, the cell lysate, wash buffer(s), elution buffer(s), etc. may be added to the extraction cartridge manually. Fluids may be moved through the extraction cartridge with gravity flow, centrifugation, positive pressure, negative pressure or the like. In another embodiment, the extraction cartridge may be inline in a liquid chromatography system and the wash buffer(s), elution buffer(s), etc. may be added to the extraction cartridge by a pump.

Following contacting the lysate with the chromatography medium, the method may further include selectively eluting the proteins bound to the chromatography medium. The elution protocol used may be dependent to at least some extent on the chemistry of the chromatography medium or the chemistry of the proteins bound to the chromatography medium. In an exemplary embodiment, the chromatography medium is a hydrophobic interaction media (e.g., a reverse phase media) and the elution buffer is an aqueous/organic mixture. For example, the elution buffer may include water and acetonitrile in a range of about 5 vol % acetonitrile to about 75 vol % acetonitrile (e.g., about 10 vol % acetonitrile to about 60 vol % acetonitrile). In one embodiment, the proteins on the extraction cartridge are eluted isocratically.

That is, proteins may be eluted from the extraction cartridge in a stepwise fashion. For instance, aqueous buffers containing 20%, 40%, and 60% acetonitrile may be added to the extraction cartridge and eluted fractions may be collected. In another embodiment, a buffer gradient with increasing acetonitrile concentration (e.g., 10 vol % acetonitrile to 60 vol % acetonitrile) may be flowed through the extraction and eluted fractions may be collected.

Following the step of selectively eluting the proteins bound to the chromatography medium, the method may further include a step of subjecting at least one eluted fraction to protein mass spectrometry analysis (e.g., one of MALDI, ESI-MS, or ESI-MS/MS).

Example 2

Described below is a kit for identifying a microorganism that may include an extraction cartridge (e.g., a single-use extraction cartridge) like the one described above. The microorganism (e.g., an infectious agent) may be in a fluid that includes interfering mammalian proteins and proteins from the microorganism.

The kit may include a sample lysis tube comprising a detergent (e.g., a detergent dried in the tube) selected for selectively lysing mammalian cells in the sample and not cells of the microorganism to be identified, a microorganism lysis buffer, and a single-use extraction cartridge comprising a chromatography medium for rapid and selective separation of mammalian proteins from microbial proteins. The kit further includes instructions for identification of the microorganism in a fluid by lysing mammalian cells in the bodily fluid; lysing cells of the microorganism; separating proteins of the microorganism from mammalian proteins using the extraction cartridge; and identifying the microorganism by subjecting proteins of the microorganism to mass spectrometry analysis.

In one embodiment, the kit further includes an elution buffer selected for eluting at least one eluted fraction off of the extraction cartridge comprising a microbial protein sufficient for identification of the microorganism. For example, the elution buffer may include water and acetonitrile in a range of about 5 vol % acetonitrile to about 75 vol % acetonitrile (e.g., about 10 vol % acetonitrile to about 60 vol % acetonitrile).

Example 3

Figure 4:
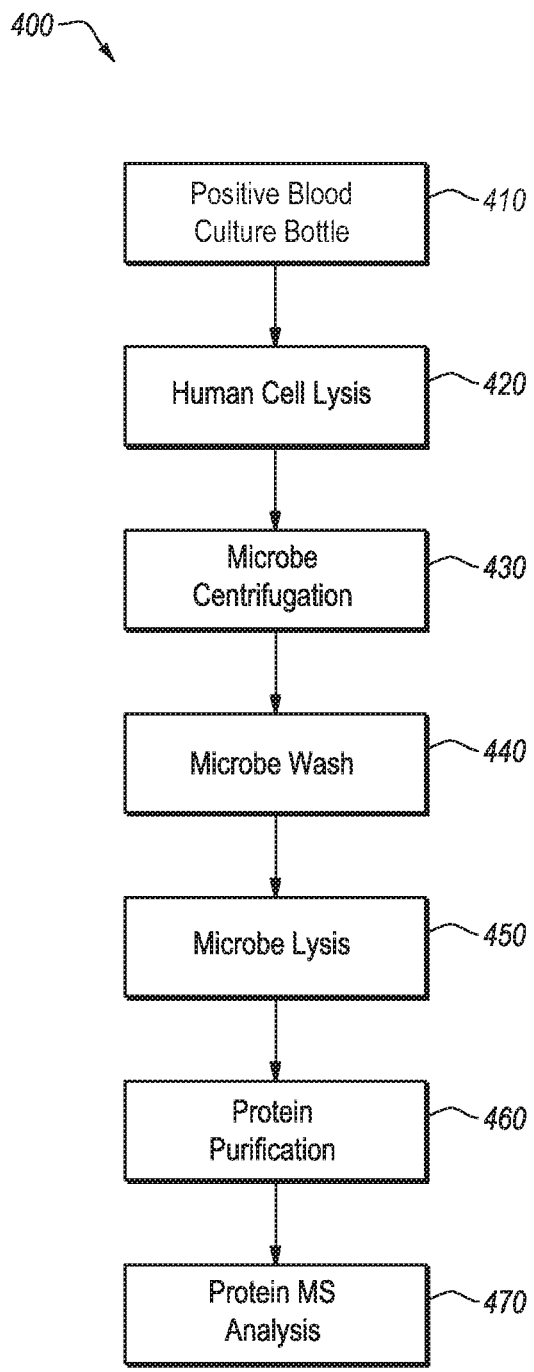
FIG. 4 is a flowchart of blood culture workflow useful in certain embodiments of the present disclosure.

Referring now to FIG. 4, a specific method of the present disclosure. The method illustrated in the flowchart of FIG. 4 relates specifically to a method for separating proteins of a microorganism from a hemoglobin in a lysate derived from a positive blood culture. Nevertheless, while the method illustrated in FIG. 4 is described in relation to blood culture, the method of FIG. 4 is applicable to other sample types such as, but not limited to, urine, cerebrospinal fluid, and whole blood. The method is also applicable to pure or mixed culture derived from clinical samples including, without limitation, pus, lacrimal fluid, nasal discharge, lymph, synovial fluid, stool sputum, wound and body site swabs, and to samples derived from other sources including industrial or environmental samples such as food (e.g., meat and dairy samples, fruits, and vegetables), beverage, soil, water (e.g., municipal waste water), air, and swabs of surfaces.

Blood is a good example for the applicability for the methods described herein because blood is one of the most challenging matrices for identification of proteins by mass spectrometry. Likewise, identification of microbes from positive blood culture bottles of patients suspected to have sepsis is one of the most important workflows in clinical microbiology and critical for patient care. Microbes can be identified by mass spectrometry (MS) using intact proteins as analytes, as been shown using either MALDI or ESI instruments. The positive blood culture sample is a very complex and challenging matrix, including human blood cells, plasma and media components in addition to the target micro-organism.

The method illustrated in FIG. 4 includes an SPE tip to purify intact proteins prior to MS analysis. Proteins from the microbial extract are bound to the SPE tip, where they are washed and later eluted into MS analysis. Using an LC gradient of increasing organic (e.g., acetonitrile (ACN)), to separate proteins bound to the tip, microbial proteins can be separated from human Hemoglobin.

Human hemoglobin (Hb) is the main component interfering MS analysis of blood culture samples. When human red blood cells are lysed, the Hemoglobin is released to the liquid in concentrations near 100 mg/ml. Human hemoglobin consists of two polypeptide chains, alpha ($\alpha$) and beta ($\beta$) chains. Since human hemoglobin is bound to many microbes using an active binding mechanism, even washing the microbial pellet does not remove the contaminating protein effectively. Surprisingly and unexpectedly, it was found that the SPE tip described elsewhere herein in greater detail could be used to rapidly separate hemoglobin from bacterial peptides. For instance, the sample preparation of workflow 400 can be accomplished in about 10-15 minutes and the mass spectrometry analysis can be accomplished within a few minutes, for example, less than 10 minutes, less than 5 minutes or within about one minute or less.

Workflow 400 includes a first step 410 of providing a positive blood culture. Whole blood may be cultured according to accepted practices in the art. Typically, blood is collected in at least two separate sterile bottles and mixed with media for aerobic and anaerobic culture. Samples scored as positive for microbial growth may be submitted for additional analysis according to workflow 400.

Referring now to step 420 of the method 400, the method further includes a step of lysing the human cells (i.e., red blood cells, platelets, white blood cells, etc) present in the sample. In the illustrated embodiment, the human cells are lysed by contacting the cells with saponin followed by sonication. In one embodiment, the saponin may be dried onto the walls of the tube used to prepare the lysate. Addition of the blood culture to the tube rehydrates and activates the saponin. While saponin is used in this example, one will appreciate that other lysing agents may be used, such as, but not limited to, certain detergents (e.g., nonionic, anionic, cationic, zwitterionic detergents).

Following lysis of the mammalian cells, step 430 includes separation of the microorganism cells from the mammalian cells by centrifugation at, for example, 12,000×g for 2 minutes and subsequently disposing of the supernatant. Step 440 may further include washing the cells of the microorganism to wash away proteins derived from the mammalian cells (e.g., hemoglobin). Washing may be accomplished by, for instance, resuspending the cells of the microorganism in a suitable buffer (e.g., phosphate+EDTA buffer, TRIS buffer, or the like) with the help of sonication and then repelleting them by centrifugation. Washing may be repeated as many times as deemed necessary (e.g., twice).

Following washing in step 440, the cells of the microorganism may be lysed to release the contents thereof in step 450. Lysis of the microorganism cells may be accomplished by any means known in the art. Disruption of microorganisms (e.g., bacterial, fungal, *mycoplasma* cells, viruses, and the like) may be achieved by mechanical, chemical, enzymatic and other means as are commonly known in the art. Mechanical approaches include bead beating, use of pressure like French press and the like, sonication, grinding, or other methods known in the art. Chemical methods include exposure to detergents or chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution. IN the illustrated embodiment of step 450, the microorganism cells are lysed by addition of a volume (e.g., 100 µl) of an aqueous solution containing approximately 50% formic acid and 25% ACN, sonication for 45 seconds, addition of another volume (e.g., 100 µl) of 50% CAN, and centrifugation for 5 min. at 12,000×g.

Proteins may be purified in step 460 for mass spectrometry analysis by collecting a volume of the supernatant from step 450, diluting (e.g., 5×, if necessary), and loading the clarified lysate onto an SPE cartridge. The chromatography medium of the SPE cartridge may be selected to selectively bind either the interfering proteins, the proteins from the at least one microorganism, or both. Likewise, the chromatography medium may be selected to selectively at least partially clean or purify the proteins from the at least one microorganism so that the at least one microorganism can be identified by mass spectrometry (e.g., MALDI or LC/MS). Suitable example of chromatography media include, but are not limited to, ion exchange media, affinity chromatography media, size exclusion media, hydrophobic interaction media, and combinations thereof. In one embodiment, the extraction cartridge is a single-use, disposable cartridge. The extraction cartridge may be loaded, washed, eluted from, etc. manually or the extraction cartridge may include in-line in a liquid chromatography system.

Purifying the proteins of the microorganism in step 450 may further include adding the lysate to the extraction cartridge and allowing the lysate to flow through the bed of chromatography media, and adding a wash buffer to the extraction cartridge and allowing the wash buffer to flow through the bed of chromatography media. The lysate and the wash buffer may be allowed to passively flow through the cartridge or they may be forced through by, for example, centrifugation or positive pressure.

Purifying the proteins of the microorganism in step 450 may further include selectively eluting the proteins bound to the chromatography medium. The elution protocol used may be dependent to at least some extent on the chemistry of the chromatography medium or the chemistry of the proteins bound to the chromatography medium. In an exemplary embodiment, the chromatography medium is a hydrophobic interaction media (e.g., a reverse phase media) and the elution buffer is an aqueous/organic mixture. For example, the elution buffer may include water and acetonitrile in a range of about 5 vol % acetonitrile to about 75 vol % acetonitrile (e.g., about 10 vol % acetonitrile to about 60 vol % acetonitrile). In one embodiment, the protein(s) may be eluted in at least one fraction. For instance, protein(s) may be eluted at different elution buffer ratios (i.e., in a gradient) and collected as fractions. In another instance, protein(s) may be eluted isocratically at a selected elution buffer composition ratio and a single fraction may be collected. Likewise, protein(s) may be eluted isocratically at two or more selected elution buffer composition ratios and two or more fractions may be collected.

Following the step 460 of purifying the proteins, the method 400 may further include a step 470 of subjecting at least one eluted fraction to protein mass spectrometry analysis. Suitable examples of mass spectrometry analysis include, but are not limited to, MALDI and LC-ESI-MS.

Examples 4-7: Identification of Microorganism(S)

Example 4—Microbial Identification from Blood Culture Using LyC Enrichment and SPE-LC-ESI-MS Analysis The blood culture workflow of FIG. 4 was used to purify the blood culture samples into an extract which could be further analyzed to yield an identification of pathogens present in the sample. In the workflow, either real clinical samples or spiked samples were used as starting material. Clinical samples were provided by HUSLAB (Hospital District of Helsinki and Uusimaa Laboratory); blood samples from patients were drawn into BacT/ALERT (bioMérieux, USA) blood culture bottles and placed in a BacT/ALERT 3D (bioMérieux, USA) blood culture instrument until positive. After the results were analyzed and the hospital did not need the positive blood culture bottles anymore, they were obtained from the hospital. The time from the positive signal of the blood culture instrument to the obtaining of the samples varied from one day (*Escherichia coli* and *Staphylococcus aureus*) to seven days (for some yeasts and more rare pathogens). Spiked samples were made in the laboratory using donated blood and strains from the in-house culture collection. Bacteria from the culture collection were revived on suitable culture plate, such as sheep blood agar, FAA agar, Sabouraud dextrose agar or chocolate agar by incubating at 35° C. overnight or at 30° C. over weekend. Anaerobic bacteria were grown under anaerobic conditions (using for example AnaeroGen 2.5 L. Oxoid, UK) and *H. influenzae* under CO2 atmosphere (using for example Pack-CO2, Mitsubishi Gas Chemical Company. Japan). Agar plates were commonly from Tammer-Tutkan Maljat, Finland.

To produce spiked samples, usually one colony from the cultivated agar plates was touched with 1 µl loop and inoculated into 8 ml of blood. The spiked blood was then injected into a blood culture bottle. For example, BacT/Alert FA Plus aerobic or BacT/Alert FN Plus anaerobic blood culture bottles (both bioMérieux, France) were used for aerobic and anaerobic microorganisms, respectively. Blood culture bottles were incubated in a blood culture instrument, such as BacT/ALERT 3D 60, bioMérieux, USA; VersaTrek, Thermo Fisher Scientific, USA or BD BACTEC 9050, Becton Dickinson, USA, until detected positive.

The sample was then transferred from a positive blood culture bottle into a sample vial for lysis plus centrifugation (LyC) enrichment. Blood culture sample volumes ranging from 100 µl to 500 µl were commonly used. Several different species and strains were tested, including Gram-positive bacteria, Gram-negative bacteria and yeasts. These included, but were not limited to, common sepsis-related pathogens such as *Staphylococcus aureus, Streptococcus pneumoniae, Escherichia coli, Pseudomonas aeruginosa* and *Candida albicans*. The sample vial was prepared with 0.1% saponin which had been dried to the sample vial wall during one night drying in the hood. Saponin was used to lyse the red blood cells and to release hemoglobin from them. Two washing/centrifugation steps were performed to remove the empty red blood cells and hemoglobin from the sample. Specifically, the vial was centrifuged for 2 minutes at 12,000×g (MicroCL 21 Centrifuge, Thermo Fisher Scientific, Germany), in order for the microorganism(s) to form a pellet and the lysed red blood cells and their released hemoglobin to stay in the supernatant as the lighter components. At this stage, the pellet was still highly concentrated with red blood cells and other proteins from the blood culture which might interfere with the further analysis methods. To remove as much of these proteins as possible, washing steps were needed. First, the supernatant was removed by pipetting and then a volume ranging from 100 to 300 µl of washing buffer, such as 10 mM $NaHPO_4$+1.8 mM $KH_2PO_4$+1 mM EDTA (pH ~7.2), was added to the vial. The pellet was broken down by sonication (12 s on, 5 s off 12 s on: 100% amplitude, a force of 3 N). To remove the empty red blood cells and to get the microorganisms to form a pellet, the vial was centrifuged (30 s; 12,000×g) and the supernatant again removed by pipetting. This wash cycle was usually repeated two times to achieve more pure end result.

The enrichment and washing phase was followed by a lysing phase, where the microbes were broken down. After the final centrifugation of the wash cycle, supernatant was removed by pipetting and 100 µl of lysis buffer (50% FA/25% ACN in H2O) was added, followed by mixing. 100 µl of storage buffer (50% ACN in H2O) was added and the vial was centrifuged (5 min; 12,000×g). Finally, the extract was collected into a protein LoBind tube (Eppendorf, Germany) and stored in −80° C. until further analysis.

For the solid phase extraction (SPE)-liquid chromatography (LC)-electrospray (ESI)—mass spectrometry (MS) analysis, 10 µl of extract derived from the lysis and centrifugation protocol was diluted with 40 µl of LC/MS compatible water (Thermo Fisher Scientific, USA) to achieve a 1:5 dilution. The sample was then concentrated by a SPE column which allowed a removal of salts and some of the small molecules in the sample. The SPE material was wetted with 50 µl of 0.2% FA (Thermo Fisher Scientific. Spain) in ACN (Thermo Fisher Scientific, UK), followed by a 2 min centrifugation at 2,000×g (Eppendorf, Germany). Equilibration of SPE was achieved by adding 50 µl of 0.2% FA into SPE after which the SPE column was centrifuged at 2,000×g for 2 min. After SPE preparation, 50 µl of the diluted sample was fed into the column and the column was washed with 50 µl of 0.2% FA in 10% ACN. After both the sample adding and washing, the column was again centrifuged (2,000×g, 2 min). The sample was then analyzed with MS.

The SPE column containing the sample was placed in an LC autosampler and LC-ESI-MS analysis was started. Solvent A was composed of 0.1% formic acid and 10% ACN in water and solvent B was composed of 0.1% formic acid in ACN. Elution of the proteins was achieved with 8 min ACN gradient (2 to 33% B) through the column. Eluting proteins were ionized using ESI source and analyzed with Q Exactive HF mass spectrometer (Thermo Fisher Scientific, Germany). Acquired MS and MS/MS data was searched with Proteome Discoverer software (version 2.0) with ProSight PD nodes (Thermo Fisher Scientific, Germany).

Figure 5A:
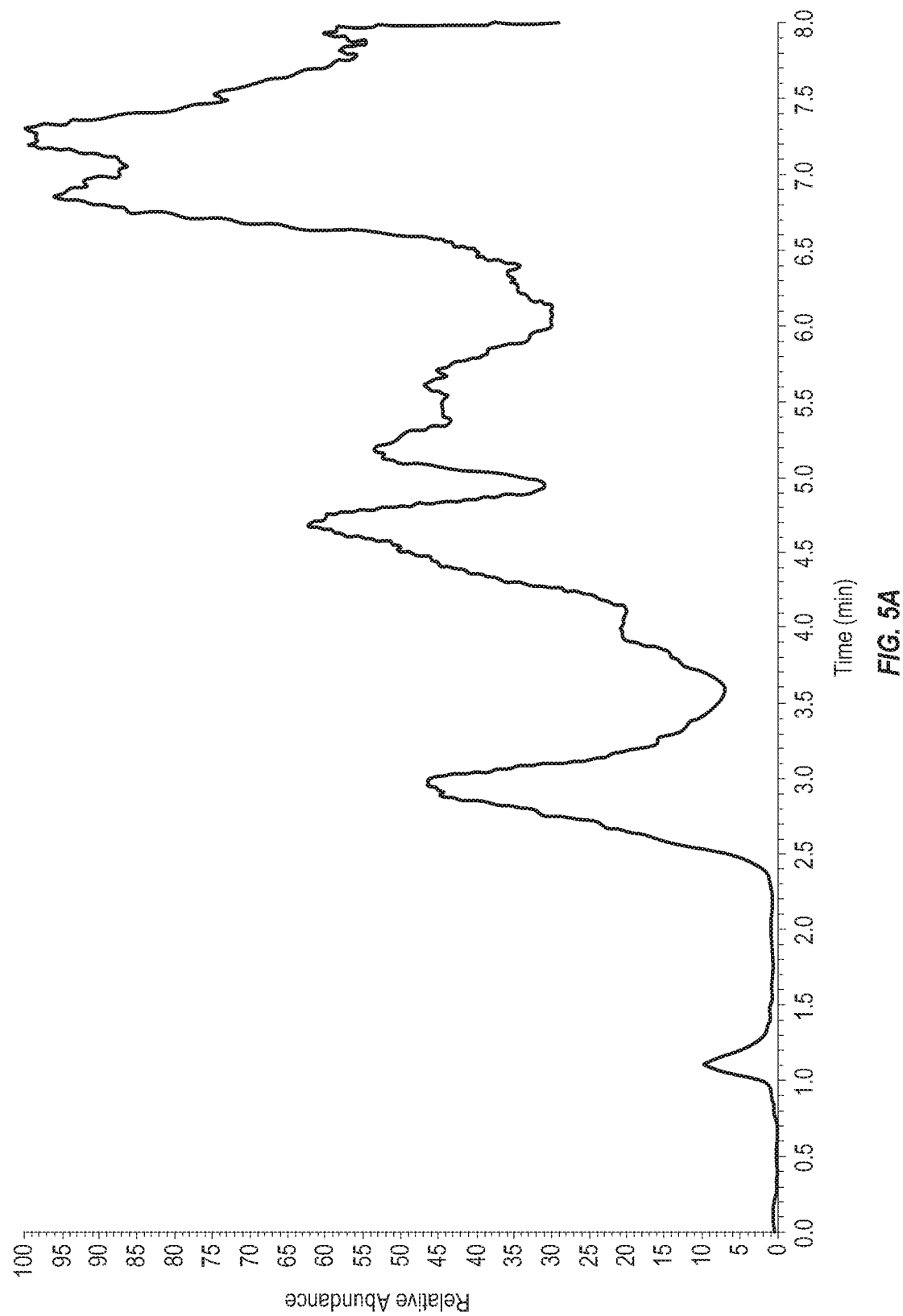
FIGS. 5A-5D illustrate analysis of microbial proteins by LC-ESI-MS, following sample preparation according to the workflow described in the present disclosure. Total ion chromatogram of the analysis is shown in FIG. 5A.
Figure 5B:
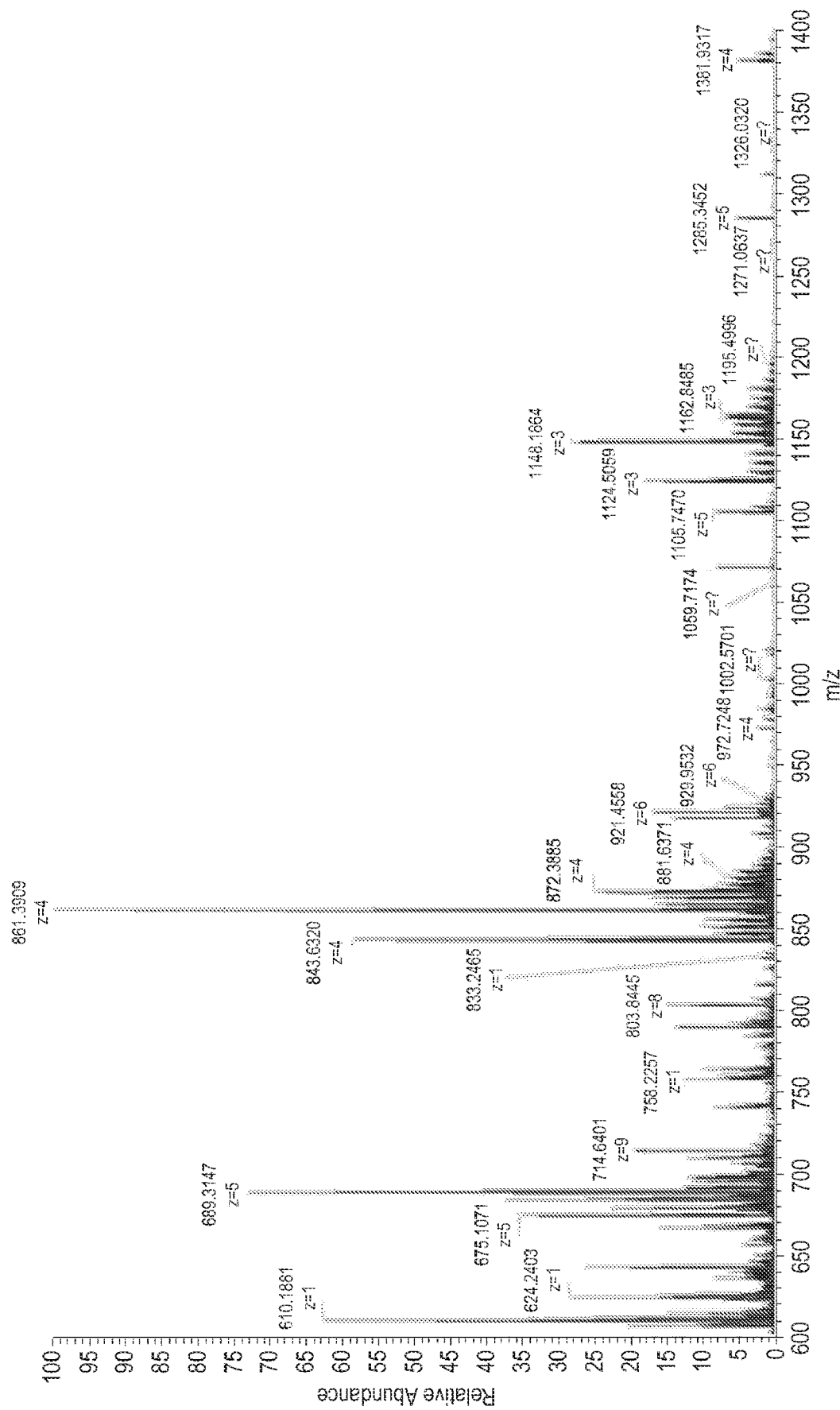
Figure 5C:
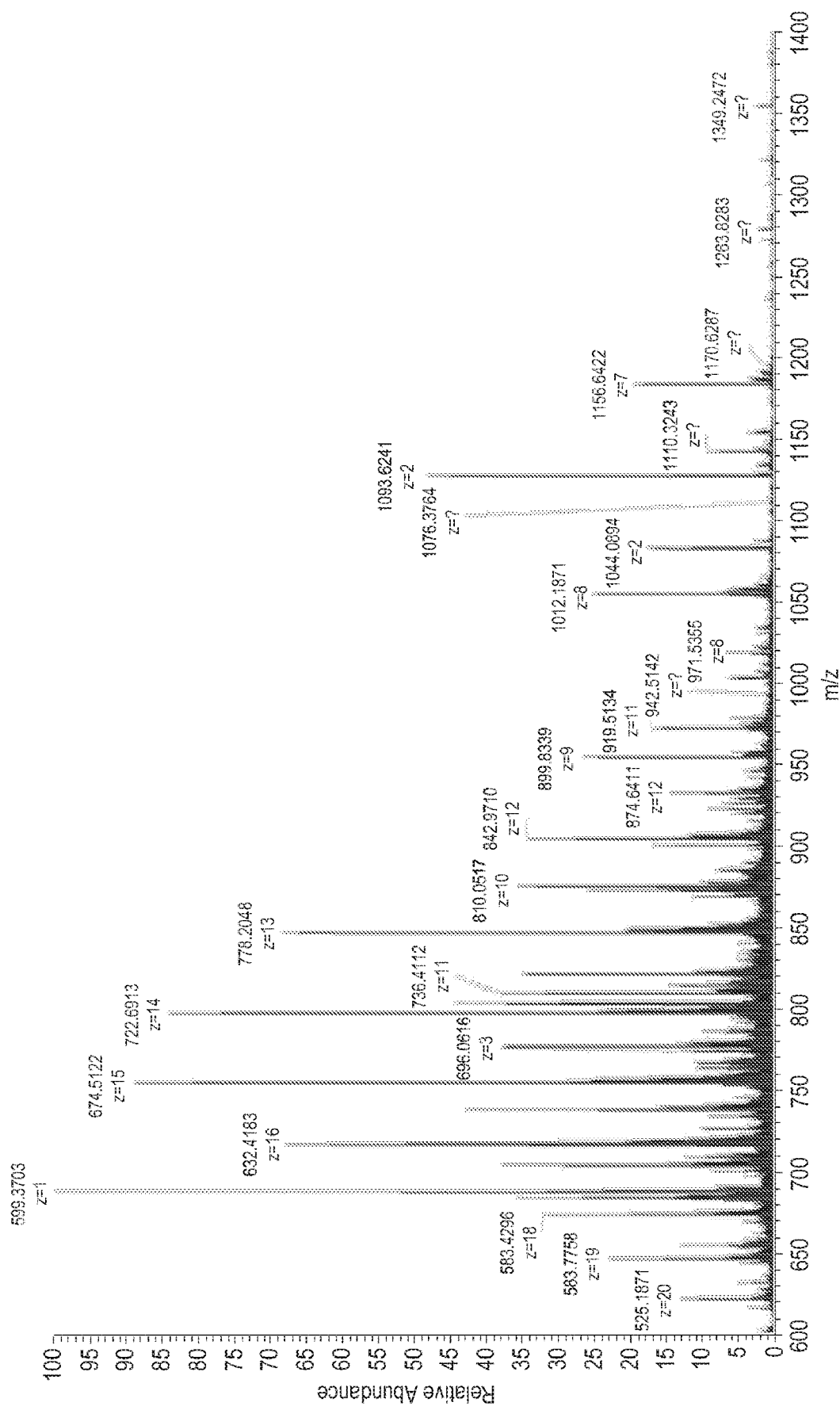
Figure 5D:
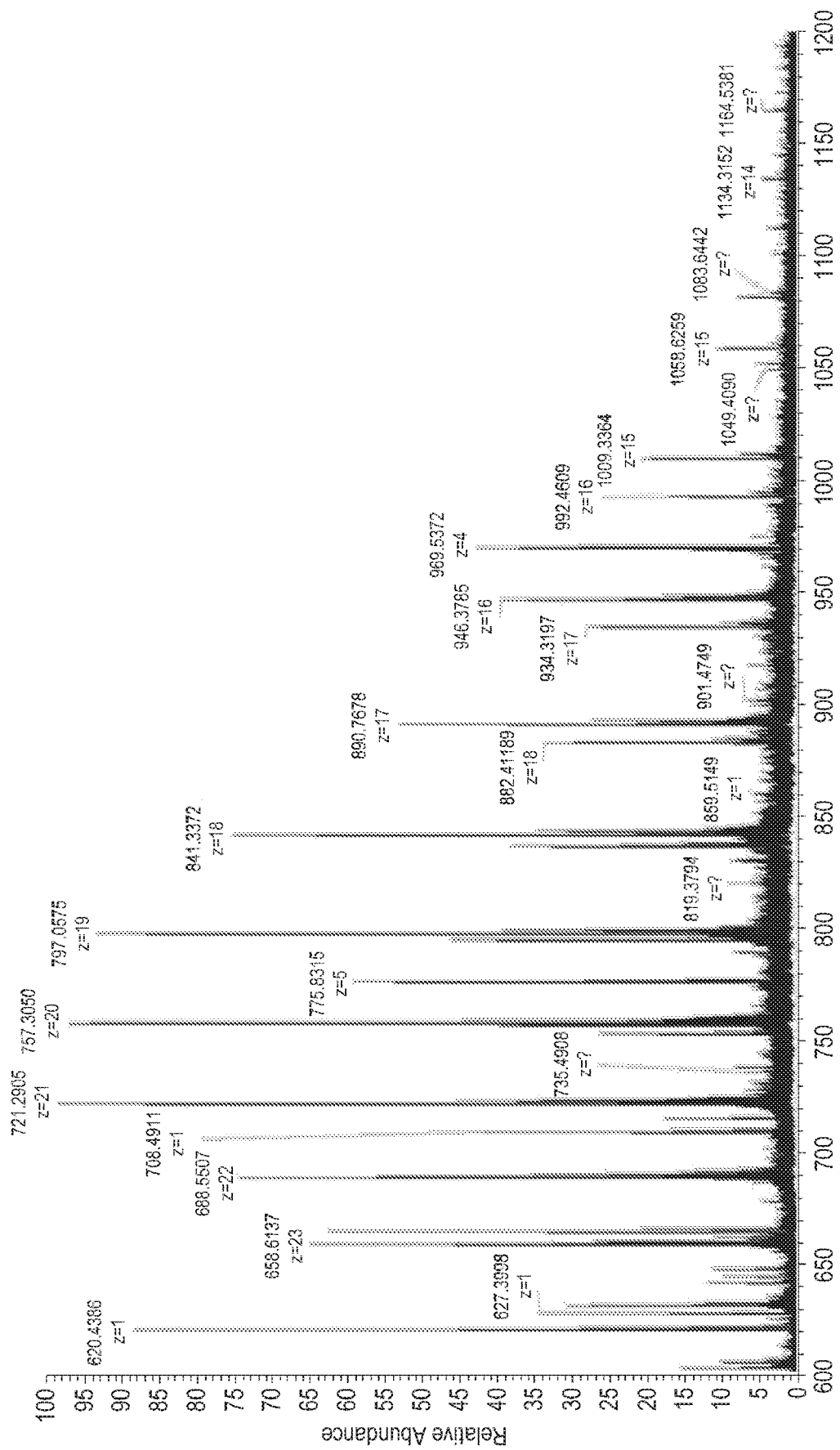

A 100 µl sample was taken from a positive blood culture bottle (containing *S. aureus*) and prepared following the protocol described above. In FIGS. 5A-5D are shown total ion chromatogram (FIG. 5A) and three example MS spectra (FIGS. 5B-5D) of blood culture sample analyzed by LC-ESI-MS showing separation of proteins of human origin from bacterial proteins. FIG. 5B shows human alpha-defensins eluting at 1.8 min. FIG. 5C shows bacterial proteins eluting at 4.0 min. FIG. 5D shows human hemoglobin alpha and beta chains eluting at 7.5 min.

Figure 6A:
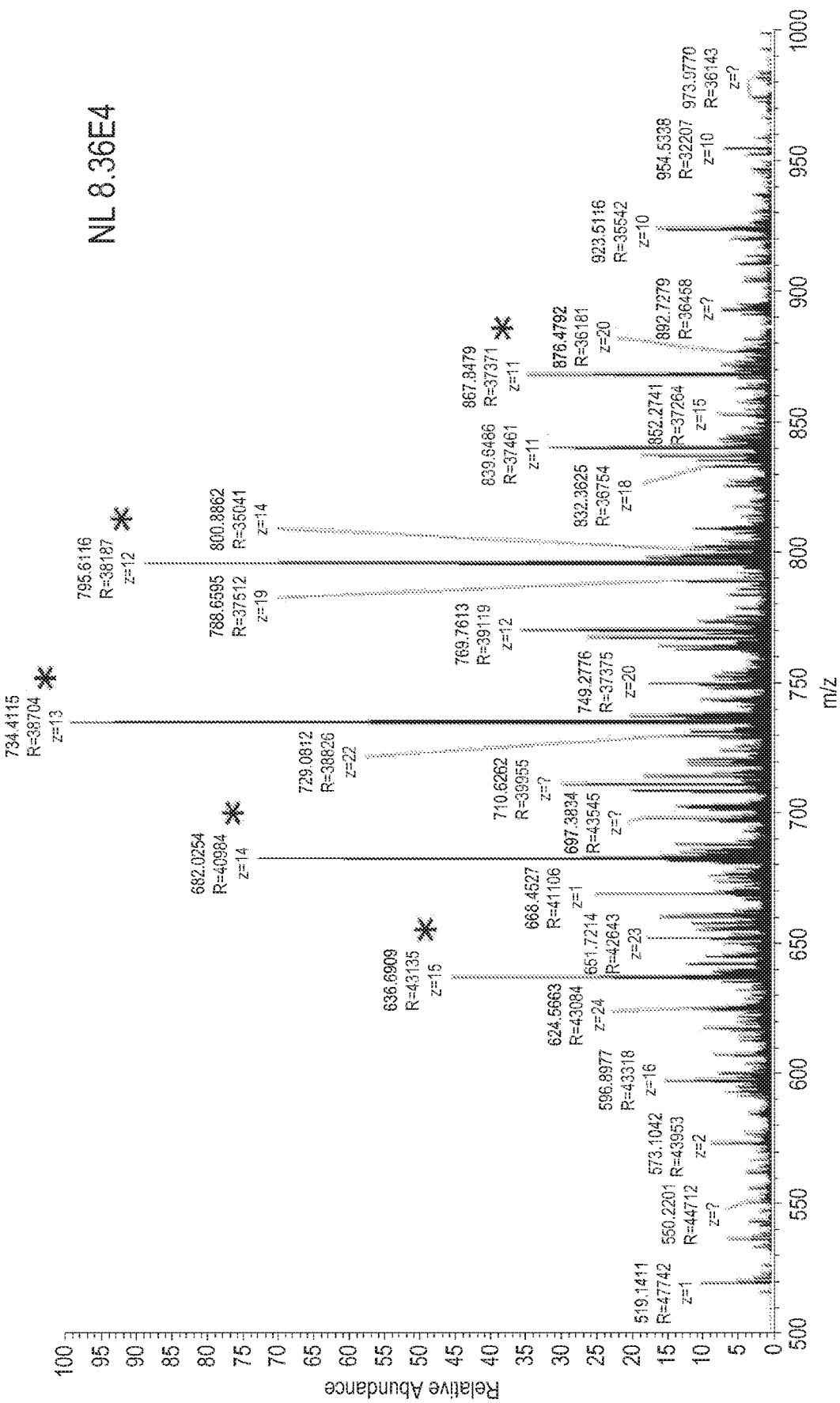
FIGS. 6A-6D illustrate ESI-MS analysis of intact microbial proteins purified in SPE tip. Intact proteins from *Escherichia coli* positive blood culture sample were bound into SPE tip and analyzed by ESI-MS using different ACN concentrations—15% (A), 17.5% (B), 20% (C) or 40% (D)—as an eluate in direct infusion MS analysis. Depending on ACN concentration different amount of microbial proteins (marked with *) and human hemoglobin (marked with a) can be seen.
Figure 6B:
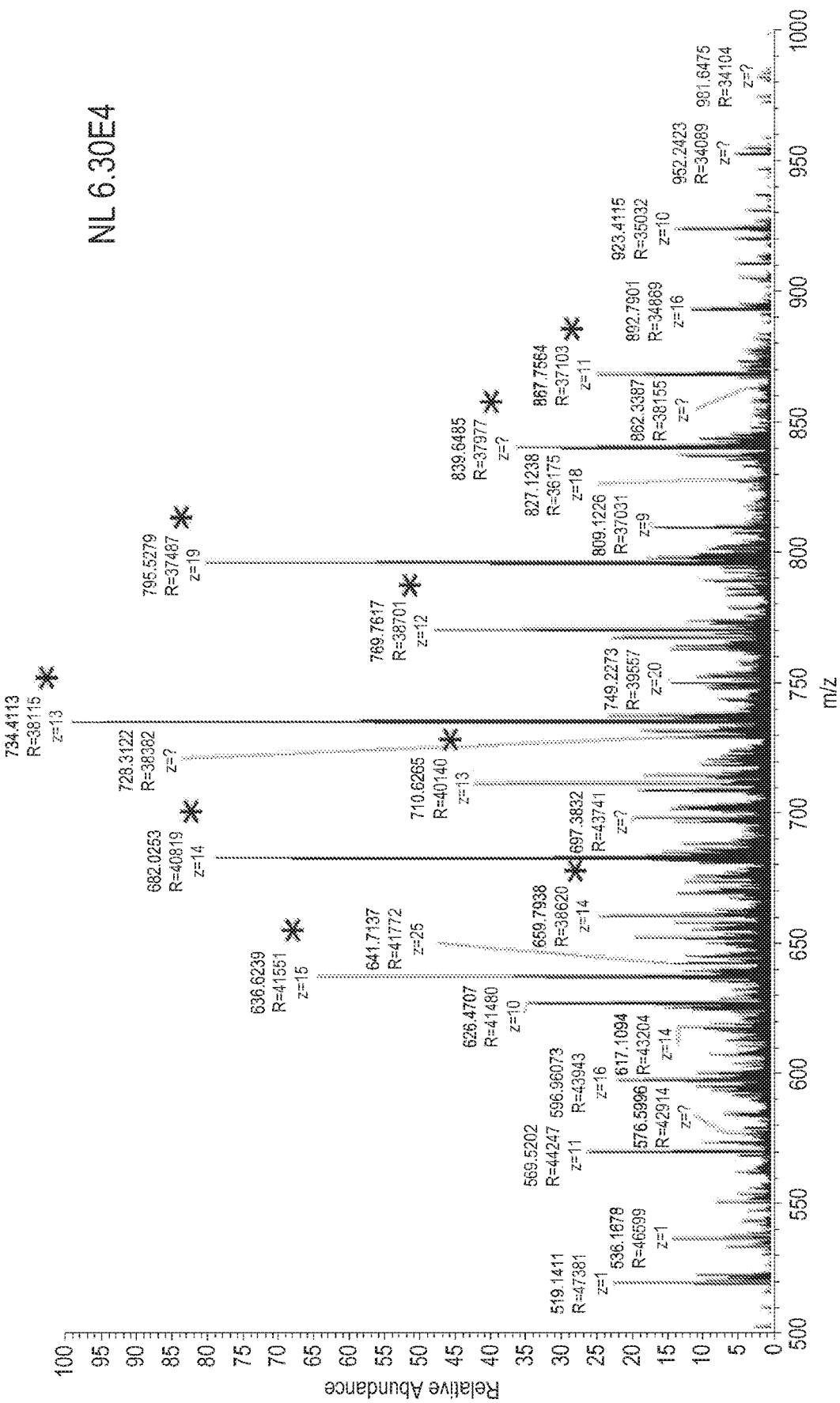
Figure 6C:
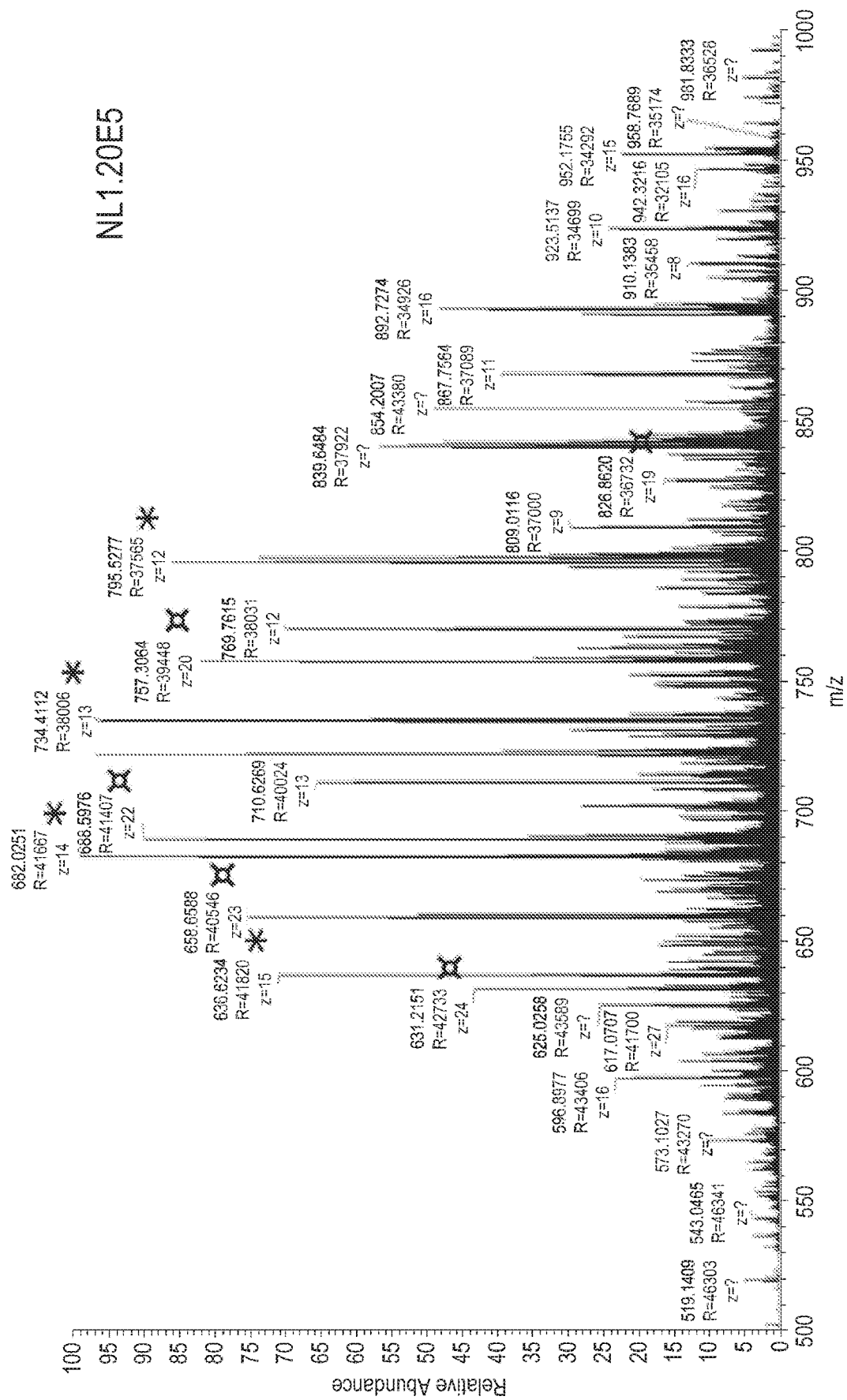
Figure 6D:
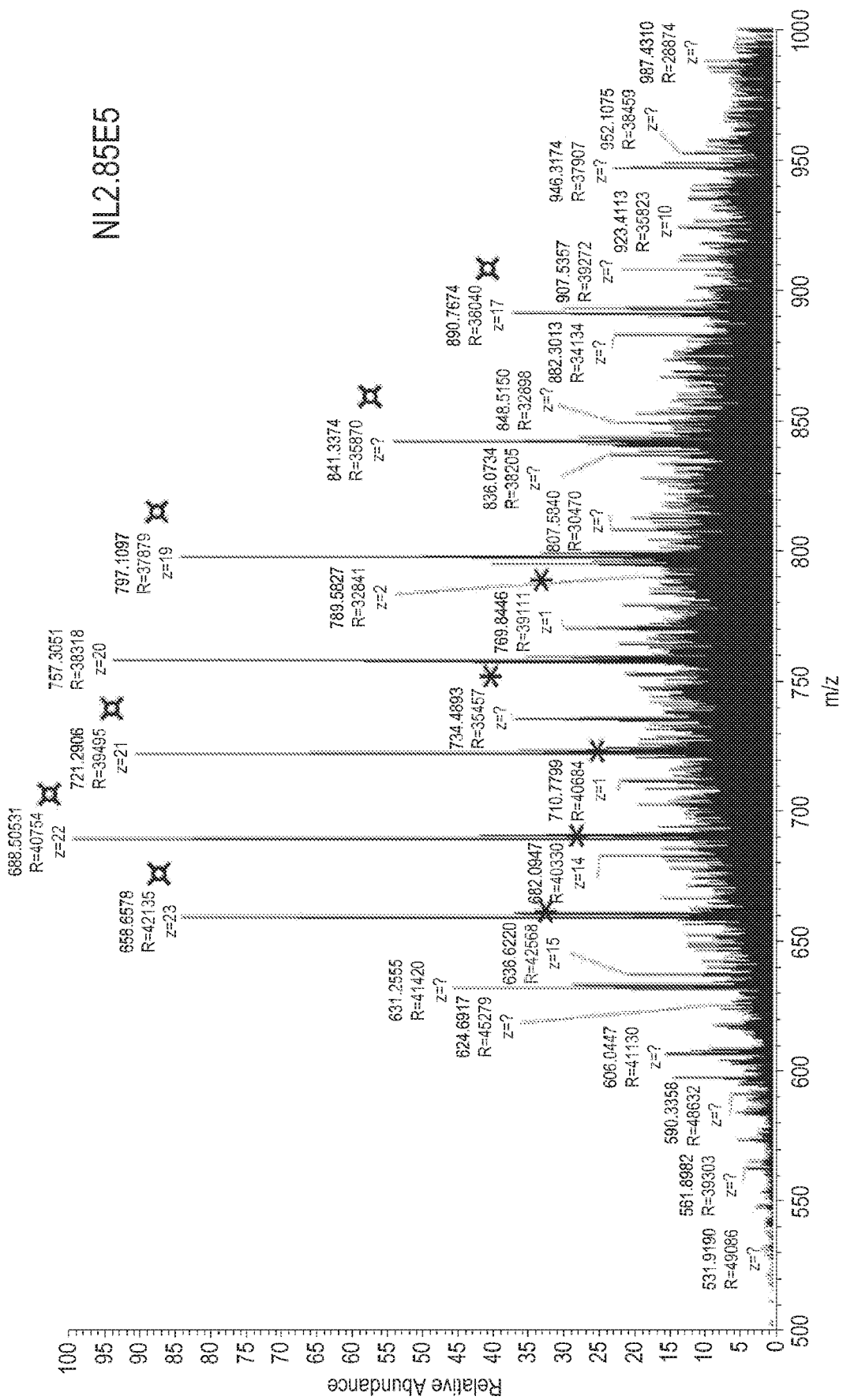

Intact proteins from *Escherichia coli* positive blood culture sample were bound into SPE tip as described above. The proteins were eluted out using 15% ACN (FIG. 6A), 17.5% ACN (FIG. 6B), 20% ACN (FIG. 6C), or 40% ACN (FIG. 6D) and analyzed by ESI-MS and direct infusion. In FIG. 6A, mostly microbial proteins can be seen eluting with 15% ACN, but with low intensity (not selected for further tests). In FIG. 6B, microbial proteins eluting with 17.5% ACN can be seen, again in relatively low quantity, but no human hemoglobin is eluted. In FIG. 6C, microbial proteins and human hemoglobin alpha chain are both visible eluting with 20% ACN, but human hemoglobin in lower amount than the most abundant microbial proteins. Intensity of the peaks is overall higher. In FIG. 6D, human hemoglobin is the most abundant protein eluting with 40% ACN and only a few microbial proteins are visible due to the suppression effect caused by the high abundance of hemoglobin.

Example 5—Microbial Identification Using LyC Enrichment and Comparing SPE-LC-ESI-MS Versus MALDI Analysis To compare the efficiency of the MALDI Sepsityper Kit (Bruker Daltonics) with the Lysis+Centrifugation method (LyC) including the SPE tip (Thermo Fisher Scientific) a challenging set of microorganism was tested. This included, but was not limited to, common sepsis-related pathogens such as *Escherichia coli, Staphylococcus aureus, S. epidermidis, S. lugdunensis* and *Streptococcus viridians, S. agalactiae, S. pyogenes.*

A sample of the microorganism, grown in VersaTREK Redox blood culture bottles (Thermo Fisher Scientific, USA), was taken and processed by a) following the MALDI Sepsityper Kit—Instructions for Use and b) the LyC method, respectively. Both methods were performed in triplicates. In the Sepsityper Kit workflow the sample was eluted after protein precipitation either in 25 µl 70% FA+25 µl ACN, which would result in an equal volume to the LyC+SPE extraction volume, or in 12.5 µl 70% FA+12.5 µl ACN, which would result in a 2× concentration compared to LyC+SPE extraction. The LyC method was performed with 100 µl starting material following the, in this patent described, protocol.

For the ESI mass spectrometric analysis, 10 µl of extract derived from the lysis and centrifugation protocol was diluted with 40 µl of LC/MS compatible water (Thermo Fisher Scientific, USA) to achieve a 1:5 dilution. The sample was then concentrated by a solid-phase extraction (SPE) which allowed a removal of salts and some of the small molecules in the sample. The SPE material was wetted with 50 µl of 0.2% FA (Thermo Fisher Scientific, Spain) in ACN (Thermo Fisher Scientific, UK), followed by a 2 min centrifugation at 2,000 rpm (3 768 G) (Eppendorf, Germany). Equilibration of SPE was achieved by adding 50 µl of 0.2%

FA into SPE after which the SPE column was centrifuged at 2,000 rpm for 2 min. After SPE preparation, 50 μl of the diluted sample was fed into the column and the column was washed with 50 μl of 0.2% FA in 10% ACN. After both the sample adding and washing, the column was again centrifuged (2,000 rpm. 2 min). After washing the SPE tip was placed in clean Eppendorf tube and 5 μl elution solution was added. Four acetonitrile concentrations (17.5%, 20%, 40% and 60% in 0.2% FA) was used. The column was centrifuged 11,000×g (Thermo Scientific Micro CL21 Centrifuge) for 15 seconds to elute the sample. Samples were taken on ice blocks to United Medix Laboratories, Helsinki, Finland (YML) by car right after elution.

The resulting extracts of both methods was applied to bioMerieux Vitek MS instrument. 0.5 μl sample was taken to MALDI plate and added 1 μl VITEK MS-CHCA matrix for use with VITEK® MS (REF 411071). Analyses were performed by YML according to bioMerieux MALDI procedure. The microbial identification via bioMerieux Vitek MS instrument is based on ID scoring. A score above 90% indicates a correct identification.

Table 1: Comparison of the results analyzed with MALDI-TOF followed the sample preparation using a commercially kit (Sepsityper, Bruker Daltonics) for blood culture samples and the workflow described in this patent (LyC+SPE tip). Intact proteins from eight positive blood cultures were bound to SPE tip and eluted using either 17.5%, 20%, 40% or 60% ACN. All eluates were analyzed using the bioMerieux Vitek MS MALDI instrument. The final results (bacterial identification) are reported by following coding: white field=no bacterial identification, −=wrong bacterial identification, +=ID score 60<x<90 and ++=ID score ≥90. In spite of similar initial sample preparation between the Sepsityper kit and the method of the present disclosure, the addition of the SPE extraction cartridge improves likelihood of correct identification of the subject microbes to a surprising and unexpected degree. Likewise, these data indicate that there is preferred but relatively broad range (e.g., about 20-40% ACN) in which the bacterial proteins can be eluted from the SPE extraction cartridge for removal of the interfering mammalian proteins, allowing for definitive identification of the bacteria by MALDI.

TABLE 1

| | ID - Sepsityper kit (Bruker) | | | | | |
|---|---|---|---|---|---|---|
| | equal volume | | | 2 x volume | | |
| Microbe | 1 | 2 | 3 | 1 | 2 | 3 |
| *Escherichia coli* | | | | | | ++ |
| *Streptococcus viridans* | | | | | | |
| *Staphylococcus aureus* | | ++ | | ++ | ++ | |
| *Staphylococcus epidermidis* | | | | ++ | ++ | ++ |
| *Staphylococcus aureus* | | | | | | |
| *Streptococcus agalactiae* | | | | ++ | ++ | ++ |
| *Streptococcus pyogenes* | | | | | | |
| *Staphylococcus lugdunensis* | | | | | | |

| | ID - LyC method + SPE tip (Thermo Fisher) | | | | | | | | | | | |
|---|---|---|---|---|---|---|---|---|---|---|---|---|
| | 17.5% ACN | | | 20% ACN | | | 40% ACN | | | 60% ACN | | |
| Microbe | 1 | 2 | 3 | 1 | 2 | 3 | 1 | 2 | 3 | 1 | 2 | 3 |
| *Escherichia coli* | | | | ++ | | | ++ | ++ | ++ | ++ | ++ | ++ |
| *Streptococcus viridans* | | ++ | ++ | − | ++ | ++ | | − | | | − | − |
| *Staphylococcus aureus* | ++ | | | ++ | ++ | ++ | ++ | ++ | ++ | ++ | ++ | ++ |
| *Staphylococcus epidermidis* | ++ | ++ | ++ | ++ | | ++ | ++ | ++ | ++ | ++ | ++ | ++ |
| *Staphylococcus aureus* | | | ++ | ++ | ++ | ++ | ++ | | ++ | ++ | ++ | ++ |
| *Streptococcus agalactiae* | + | ++ | | | | ++ | ++ | ++ | ++ | ++ | ++ | ++ |
| *Streptococcus pyogenes* | | − | | ++ | | | ++ | ++ | ++ | ++ | ++ | ++ |
| *Staphylococcus lugdunensis* | | | | ++ | ++ | − | ++ | ++ | ++ | − | ++ | ++ |

Example 6—Microbial Identification from Urine Samples Using LyC Enrichment and SPE-LC-ESI-MS Analysis The urine sample workflow was used to prepare samples leading to extracts for analysis and identification of the microbe(s) within the samples. In the workflow example, spiked samples were used as starting material. Bacteria were harvested from the agar, washed with PBS and the absorbance adjusted (A600 nm=1) yielding approximately $1 \times 10^9$ cfu/ml. The suspension was centrifuged and the pellet resuspended with urine from a healthy volunteer. Samples of 150 μl containing approximately $10^6$ cfu/ml were transferred to a sample vial, followed by similar washing and lysing phases as well as SPE-LC-ESI-MS analysis as explained in Example 4. The LC workflow used gradient of increasing content of organic solvent, which was advantageous for decreasing interference from urine compounds in mass spectra. Several bacteria and even yeasts may cause urine tract infections and this example includes *Escherichia coli* which is the most common cause to these infections.

Figure 7:
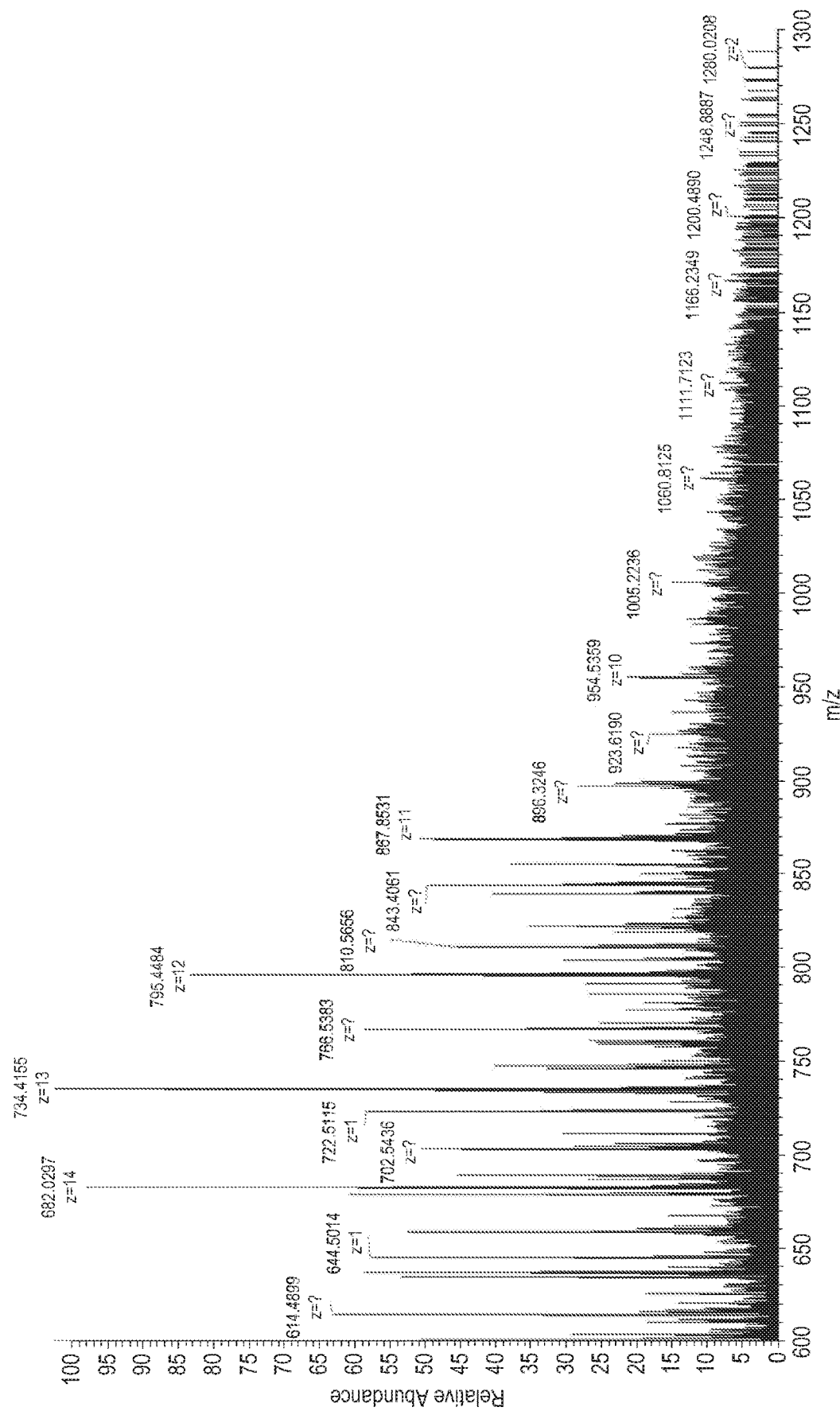
FIG. 7 illustrates a full scan electrospray mass spectrum of a urine sample containing bacteria performed via SPE-LC is illustrated. The scan ranges from m/z 600 to m/z 1300. Present in the figure are for example peaks representing different charge states of DNA-binding protein HU-alpha from *Escherichia coli* at the following m/z values: 682.03 (+14), 734.42 (+13), 795.45 (+12) and 867.85 (+11).

An example of a readout spectrum is shown in FIG. 7, and proteins identified from the sample are listed in Table 2.

TABLE 2

| Proteins identified from the urine sample | | |
|---|---|---|
| Cluster | Description | Taxonomy |
| 82581657 | DNA-binding protein HU-beta | Eco/Sfl |
| 82581652 | DNA-binding protein HU-alpha | Eco |
| 123048783 | 50S ribosomal protein L24 | Eco |
| 334305782 | Cold shock-like protein CspE | Eco/Sen |
| 259491921 | 50S ribosomal protein L33 | Eic |
| 226735184 | 30S ribosomal protein S19 | Eco |

TABLE 2-continued

Proteins identified from the urine sample

| Cluster | Description | Taxonomy |
|---|---|---|
| 259646975 | 50S ribosomal protein L30 | Eco |
| 226736319 | 50S ribosomal rotein L25 | Eco |
| 226708274 | 50S ribosomal protein L32 | Eco |

Eco = *Escherichia coli*;
Sfl = *Shigella flexneri*;
Sen = *Salmonella enterica*;
Eic = *Edwardsiella ictaluri*.
Where two taxonomies are expressed, both identifications were plausible.

Example 7—Microbial Identification Workflow with Different Solid Phase Extraction (SPE) Material A microbial sample, where the cells have been lysed and the proteins released to the solution (a microbial extract) can be further processed with solid phase extraction (SPE) in order to concentrate the proteins and to remove the small molecules and salts before analysis e.g. with mass spectrometry. Typically the SPE material is packed inside a column, tip or in the form of e.g. 96-well format. The material allows the binding of the proteins due to interactions with the material and the proteins. These interactions can be e.g. hydrophilic/-phobic interactions, ion-ion interactions or affinity to the material. The material must allow a liquid flow through the material. The sample is released from the column e.g. increasing the hydrophobicity or changing the pH of the passing solvent. This removal can be done either once, in steps or with gradient. The liquid is pushed through the column with the help of e.g. gravity, syringe, pump or centrifuge.

Test samples were prepared from extracts of *Escherichia coli*. The extract was prepared by lysing *E. coli* in a solvent containing 50 vol. % formic acid (FA) and vol. % acetonitrile (ACN). The FA and ACN concentrations were adjusted to 37.5 vol. % ACN and 25 vol. % FA. The protein concentration in the test samples was between 2 mg/ml and 3 mg/ml as determined with BCA analysis. Test samples were diluted and 1 µg to 11 µg protein was applied to the extraction columns. Extraction columns used in this test were all reverse phase columns with C8, SDB-XC or RP-4H chemistry. SDB-XC (3M) is a poly(styrenedivinlybenxene) copolymer which is spherical, porous and cross-linked. RP-4H chemistry is explained elsewhere. C8 was tested with two ThermoFisher Scientific MSIA platform and ThermoFisher Scientific StageTip platform.

Before the test samples were applied to the extraction columns, the medium was wetted with ACN having a 0.2 vol. % FA. The medium was then equilibrated with a solution containing water and 0.2 vol. % FA. Samples having a total amount of from 1 µg to 11 µg protein were pushed through the medium in the extraction column. The flow through from the samples was collected for analysis. The medium was washed with a solution containing water and 0.1-0.2 vol. % FA. Protein samples were eluted from the medium with a solution containing water, 60 vol. % ACN, and 0.2 vol. % FA. The eluted proteins were collected for analysis.

The flow through (FT) samples and eluted samples were analyzed for protein concentration. In some results, the eluates of multiple samples (3-5) were combined and partially dried to about ⅓ their original volume before being analyzed. Protein concentration was determined using the Nanodrop BCA assay (Thermo Fisher Scientific). The bovine serum albumin standard curves were prepared using the same FA and ACN concentrations as was used in the FT and eluate samples. The results are provided in Table 3.

Another experiment was performed with RP-4H tips and POROS R1 plates using extracts from *Candida tropicalis*, *C. tropicalis* extract was prepared as *E. coli* extract above, and the sample was diluted to water to 1:5 dilution (10 µl extract and 40 µl of water). Prior sample addition the SPE tip medium was wetted with 50 µl of ACN with 0.2% FA and the RP-4H tips or the POROS R1 plate were centrifuged to push the liquid through. The mediums were then equilibrated with 50 µl 0.2% FA and centrifuged again before the sample application. The sample was centrifuged and the medium was washed with 50 µl 0.2% FA before elution. The mediums were eluted with 10 µl 60% ACN with 0.2% FA to clean lo-binding containers. The eluents were then transformed to Hamilton syringe and sprayed to the mass spectrometer. FIGS. 8A-8B show the mass spectra of the RP-4H (FIG. 8B) or POROS R1 (FIG. 8A) purified *C. tropicalis*.

TABLE 3

Examples of the *E. coli* protein binding to different SPE-tip materials.

| Tip | Applied prot. amount (µg) | Bound (µg) | Fluted (µg) | Yield (%) | Recovery (%) |
|---|---|---|---|---|---|
| RP-4H | 1.0 | 0.5 | 0.3 | 27% | 54% |
| Stage tip C8 | 11.1 | 1.4 | 1.2 | 11% | 86% |
| Stage tip SVB-XC | 11.1 | 2.3 | 2.0 | 18% | 87% |
| Poros R1 | 3.5 | 1.6 | 1.2 | 35% | 75% |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for identifying a microorganism in a fluid comprising one or more interfering mammalian proteins, the method comprising:
    preparing a lysate from the fluid, the lysate comprising a microorganism protein and an interfering mammalian protein from the group consisting of defensins and proteolysis products thereof;
    contacting the lysate with a chromatography medium, wherein hemoglobin, defensins or proteolysis products thereof and the microorganism protein bind to the chromatography medium;
    selectively eluting proteins bound to the chromatography medium to produce at least one eluted fraction, wherein the at least one eluted fraction is enriched in the microorganism protein and depleted in defensins or proteolysis products thereof; and
    subjecting the at least one eluted fraction to protein mass spectrometry analysis and thereby identifying the microorganism in the fluid.

2. The method of claim 1, wherein the fluid is urine or cerebrospinal fluid.

3. The method of claim 1, further comprising separating cell fragments and unlysed microorganism cells from the lysate.

4. The method of claim 3, further comprising:
contacting the fluid with a lysing agent selected to lyse mammalian cells in the fluid but not a microorganism cell;
separating the microorganism cell from the lysed mammalian cells; and
washing the microorganism cell.

5. The method of claim 1, wherein contacting the lysate with the chromatography medium includes:
providing an extraction cartridge that contains a bed of the chromatography medium;
adding the lysate to the extraction cartridge and allowing the lysate to flow through the bed of chromatography media; and
adding a wash buffer to the extraction cartridge and allowing the wash buffer to flow through the bed of chromatography media; and
selectively eluting proteins bound to the chromatography medium with an elution buffer.

6. The method of claim 4, wherein the extraction cartridge is inline in a liquid chromatography system and the lysate is added to the extraction cartridge by a pump.

7. The method of claim 5, wherein the elution buffer comprises water and acetonitrile in a range of 10 vol % acetonitrile to 60 vol % acetonitrile.

8. The method claim 1, wherein the protein mass spectrometry analysis is one of MALDI or ESI-MS.

9. The method claim 1, wherein the chromatography medium is selected from the group consisting of reversed-phase media, normal phase media, ion exchange media, affinity chromatography media, size exclusion media, hydrophobic interaction media, and combinations thereof.

10. The method of claim 1, wherein the chromatography medium is prepared from monomers selected from the group consisting of substituted or unsubstituted vinyl containing monomers, substituted or unsubstituted acrylate containing monomers, substituted or unsubstituted methacrylate containing monomers, acrylamide, fluoro-substituted ethylene, polymers selected from the group consisting of polyolefin, polyester, polyurethane, polyamide, and combinations thereof.

11. The method of claim 10, wherein the monomers include a mixture of at least two monomers present in an amount of from 10 vol. % to 70 vol. %.

12. The method of claim 1, wherein the chromatography medium is prepared from a mixture of any two or more of: divinyl benzene, styrene, and ethylvinylbenzene.

13. A method for identifying a microorganism in a fluid comprising one or more interfering mammalian proteins, the method comprising:
preparing a lysate from the fluid, the lysate comprising a microorganism protein and an interfering mammalian protein from the group consisting of hemoglobin, defensins and proteolysis products thereof;
passing the lysate through an extraction cartridge, the extraction cartridge comprising:
a column body having a reservoir portion, an extraction media portion, and a collar portion;
wherein the reservoir portion includes an inlet and a reservoir;
wherein the extraction media portion includes an elongated sleeve having an inner surface defining a cavity having a chromatography medium therein, said elongated sleeve further having an inlet end in fluid communication with the reservoir and an outlet end disposed remote from the inlet end, the chromatography medium extending substantially to the outlet end of the elongated sleeve;
wherein the collar portion extends axially in a common direction with the elongated sleeve and has a terminal end which is spaced apart from the outlet end of the elongated sleeve and which extends axially at least to a plane defined by the outlet end of the elongated sleeve; and
wherein the interfering mammalian protein and the microorganism protein bind to the chromatography medium;
selectively eluting proteins bound to the chromatography medium to produce at least one eluted fraction, wherein the at least one eluted fraction is enriched in the microorganism protein and depleted in hemoglobin, defensins or proteolysis products thereof; and
subjecting the at least one eluted fraction to protein mass spectrometry analysis and thereby identifying the microorganism in the fluid.

14. The method of claim 13, wherein the fluid is blood, a blood culture, urine or cerebrospinal fluid.

15. The method of claim 13, further comprising separating cell fragments and unlysed microorganism cells from the lysate.

16. The method of claim 15, further comprising:
contacting the fluid with a lysing agent selected to lyse mammalian cells in the fluid but not a microorganism cell;
separating the microorganism cell from the lysed mammalian cells; and
washing the microorganism cell.

17. The method of claim 13, further comprising, after passing the lysate through the extraction cartridge and prior to selectively eluting proteins bound to the chromatography medium, adding a wash buffer to the extraction cartridge and allowing the wash buffer to flow through the chromatography medium.

18. The method of claim 13, wherein the extraction cartridge is inline in a liquid chromatography system and the lysate is added to the extraction cartridge by a pump.

19. The method of claim 13, wherein the step of selectively eluting proteins bound to the chromatography medium comprises selectively eluting the proteins using an elution buffer that comprises water and acetonitrile in a range of 10 vol % acetonitrile to 60 vol % acetonitrile.

20. The method of claim 13, wherein the protein mass spectrometry analysis is one of MALDI or ESI-MS.

21. The method claim 13, wherein the chromatography medium is selected from the group consisting of reversed-phase media, normal phase media, ion exchange media, affinity chromatography media, size exclusion media, hydrophobic interaction media, and combinations thereof.

22. The method of claim 13, wherein the chromatography medium is prepared from monomers selected from the group consisting of substituted or unsubstituted vinyl containing monomers, substituted or unsubstituted acrylate containing monomers, substituted or unsubstituted methacrylate containing monomers, acrylamide, fluoro-substituted ethylene, polymers selected from the group consisting of polyolefin, polyester, polyurethane, polyamide, and combinations thereof.

23. The method of claim 22, wherein the monomers include a mixture of at least two monomers present in an amount of from 10 vol. % to 70 vol. %.

24. The method of claim 13, wherein the chromatography medium is prepared from a mixture of any two or more of: divinyl benzene, styrene, and ethylvinylbenzene.

* * * * *